(12) United States Patent
Lee et al.

(10) Patent No.: US 10,345,204 B2
(45) Date of Patent: *Jul. 9, 2019

(54) CONTACT-TYPE PATCH, STAINING METHOD USING THE SAME, AND MANUFACTURING METHOD THEREOF

(71) Applicant: NOUL CO., LTD., Seoul (KR)

(72) Inventors: Dongyoung Lee, Yongin-si (KR);
Kyunghwan Kim, Yongin-si (KR);
Youngmin Shin, Yongin-si (KR);
Hyunjeong Yang, Seongnam-si (KR);
Chanyang Lim, Seongnam-si (KR)

(73) Assignee: NOUL CO., LTD., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/498,343

(22) Filed: Apr. 26, 2017

(65) Prior Publication Data

US 2017/0241873 A1 Aug. 24, 2017

Related U.S. Application Data

(63) Continuation of application No. 15/206,247, filed on Jul. 9, 2016.

(60) Provisional application No. 62/298,959, filed on Feb. 23, 2016.

(30) Foreign Application Priority Data

Jun. 4, 2016 (KR) .................. 10-2016-0069936
Jun. 4, 2016 (KR) .................. 10-2016-0069937
Jun. 4, 2016 (KR) .................. 10-2016-0069938

(51) Int. Cl.
*G01N 1/31* (2006.01)
*G01N 1/30* (2006.01)

(52) U.S. Cl.
CPC ............. *G01N 1/31* (2013.01); *G01N 1/30* (2013.01); *G01N 1/312* (2013.01); *G01N 2001/302* (2013.01)

(58) Field of Classification Search
None
See application file for complete search history.

(56) References Cited

U.S. PATENT DOCUMENTS

| 555,270 | A | * | 2/1896 | Taylor ................ E02F 3/656 37/418 |
| 3,870,146 | A | | 3/1975 | Greenfield et al. |
| 4,250,257 | A | | 2/1981 | Lee et al. |
| 4,938,593 | A | * | 7/1990 | Morris ................ G01N 21/171 356/344 |
| 5,143,714 | A | * | 9/1992 | Cosgrove ............ G01N 1/30 435/182 |
| 5,552,279 | A | | 9/1996 | Weisburg et al. |
| 5,928,879 | A | | 7/1999 | Dumler et al. |
| 6,063,029 | A | | 5/2000 | Saita et al. |
| 6,174,683 | B1 | * | 1/2001 | Hahn ............... G01N 33/54353 435/6.12 |
| 7,767,414 | B1 | * | 8/2010 | Smith ............... G01N 1/30 435/1.1 |
| 8,305,579 | B2 | | 11/2012 | Treynor et al. |
| 8,628,787 | B2 | | 1/2014 | Soldani et al. |
| 8,809,027 | B1 | | 8/2014 | Lynch et al. |
| 8,936,912 | B2 | | 1/2015 | Mitra et al. |
| 2003/0083294 | A1 | * | 5/2003 | Sullenger ............. C12N 15/113 514/44 R |
| 2004/0038306 | A1 | * | 2/2004 | Agnew ................ G01N 33/50 435/7.1 |
| 2004/0175710 | A1 | | 9/2004 | Haushalter |
| 2005/0139511 | A1 | * | 6/2005 | Burns ................. B65D 79/02 206/710 |
| 2005/0175997 | A1 | * | 8/2005 | Ono ................... C12Q 1/6809 435/6.12 |
| 2005/0202567 | A1 | | 9/2005 | Zanzucchi et al. |

(Continued)

FOREIGN PATENT DOCUMENTS

KR 10-0601831 B1 7/2006
KR 10-1453796 B1 10/2014

(Continued)

OTHER PUBLICATIONS

Beck et al., "On-chip sample preparation by controlled release of antibodies for simple CD4 counting," Lab on a Chip, 2012, vol. 12, No. 1, pp. 167-173.
International Search Report dated May 29, 2017 as received in Application No. PCT/KR2017/002027.
International Search Report dated May 29, 2017 as received in Application No. PCT/KR2017/002029.
International Search Report dated May 29, 2017 as received in Application No. PCT/KR2017/002031.

(Continued)

*Primary Examiner* — Ann Y Lam
(74) *Attorney, Agent, or Firm* — Jones Day

(57) ABSTRACT

The present disclosure relates to a gel-phase patch that performs a function of assisting in staining during a staining process such as a process of coming into contact with a specimen such as blood to perform a staining function of staining the specimen, a process of fixing the specimen, or a process of forming an optimal pH at a specimen stained by a staining sample. According to an aspect of the present disclosure, a contact-type staining patch includes a staining solution that reacts with a specimen and a gel receptor provided as a gel matrix of a mesh structure in which a pore that accommodates the staining solution is formed and the mesh structure prevents the staining solution in the pore from leaking or degenerating, and having a contact surface that comes into contact with the specimen to transfer some of the staining solution to the specimen.

8 Claims, 29 Drawing Sheets

(10 of 29 Drawing Sheet(s) Filed in Color)

(56) References Cited

U.S. PATENT DOCUMENTS

| | | | |
|---|---|---|---|
| 2005/0244976 A1* | 11/2005 | Gee | C09B 23/06 436/86 |
| 2006/0088847 A1* | 4/2006 | Gu | C07K 14/4747 435/5 |
| 2006/0111331 A1* | 5/2006 | Eishingdrelo | A61K 31/58 514/176 |
| 2006/0121474 A1 | 6/2006 | Kim et al. | |
| 2007/0117177 A1* | 5/2007 | Luo | C12P 21/00 435/68.1 |
| 2007/0128073 A1 | 6/2007 | Tappen | |
| 2008/0182287 A1* | 7/2008 | Smith | A61L 31/145 435/177 |
| 2009/0098165 A1* | 4/2009 | Arulanandam | A61K 38/16 424/263.1 |
| 2009/0220968 A1 | 9/2009 | Issadore et al. | |
| 2011/0041978 A1* | 2/2011 | Wallace | G01N 33/5432 156/60 |
| 2011/0070606 A1 | 3/2011 | Winkelman et al. | |
| 2011/0257666 A1 | 10/2011 | Ladet et al. | |
| 2012/0040397 A1* | 2/2012 | Luo | A61K 9/06 435/68.1 |
| 2012/0064041 A1 | 3/2012 | Alexanian | |
| 2012/0171290 A1* | 7/2012 | Coursaget | A61K 39/0011 424/489 |
| 2013/0213811 A1* | 8/2013 | Kennedy | G01N 33/54386 204/455 |
| 2013/0288273 A1 | 10/2013 | Takagi et al. | |
| 2013/0296761 A1* | 11/2013 | Goto | A61K 9/0014 602/54 |
| 2014/0004527 A1 | 1/2014 | Oka et al. | |
| 2014/0038230 A1 | 2/2014 | Beck et al. | |
| 2015/0080252 A1* | 3/2015 | Godwin | C12Q 1/6886 506/9 |
| 2016/0265028 A1 | 9/2016 | Kim et al. | |

FOREIGN PATENT DOCUMENTS

| | | |
|---|---|---|
| KR | 10-2015-0048964 A | 5/2015 |
| KR | 10-1540845 B1 | 7/2015 |

OTHER PUBLICATIONS

International Search Report dated May 29, 2017 as received in Application No. PCT/KR2017/002026.
International Search Report dated May 29, 2017 as received in Application No. PCT/KR2017/002032.

\* cited by examiner (a)  (b)

Fig. 25
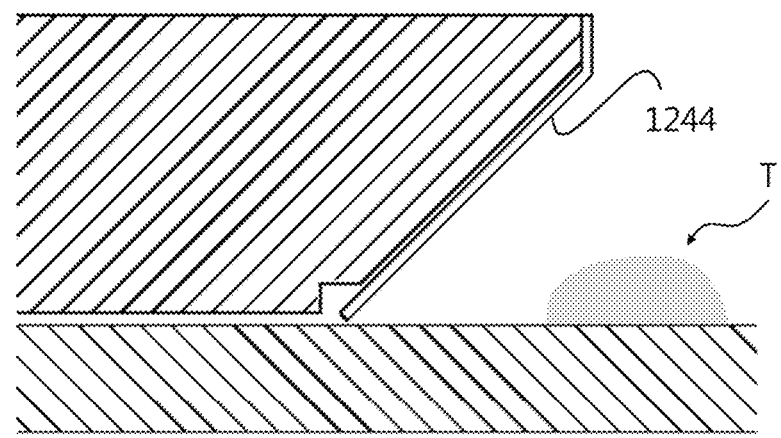
(a)
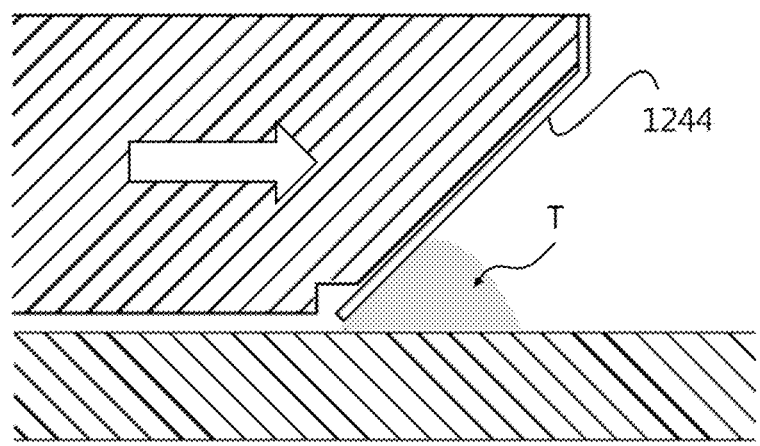
(b)
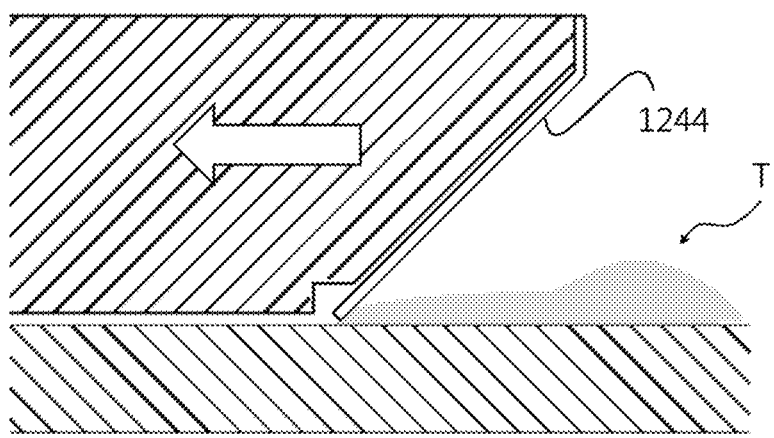
(c)

(a)          (b)          (c)

CONTACT-TYPE PATCH, STAINING METHOD USING THE SAME, AND MANUFACTURING METHOD THEREOF

CROSS-REFERENCE TO RELATED APPLICATION

This application is a continuation of U.S. patent application Ser. No. 15/206,247, filed Jul. 9, 2016, which claims the benefit of U.S. provisional patent application No. 62/298,959, filed Feb. 23, 2016 and which claims priority to Korean patent application nos. 10-2016-0069936, 10-2016-0069937, 10-2016-0069938 filed on Jun. 4, 2016. The foregoing applications are incorporated herein by reference in its entirety.

BACKGROUND

1. Field of the Invention

The present disclosure relates to a contact-type patch, a staining method using the same, and a manufacturing method thereof, and more particularly, to a gel-phase patch that performs a function of assisting in staining during a staining process by coming into contact with a specimen such as blood to perform a staining function of staining the specimen, fixing a specimen, or forming an optimal pH at a specimen stained by a staining sample, a staining method using the same, and a manufacturing method thereof.

2. Discussion of Related Art

A blood smear examination is a testing method in which blood is smeared and stained and morphologies of blood cells are observed using a microscope. A blood smear examination is mostly used in testing for infections of parasitic diseases such as malaria, blood cancers including leukemia, or congenital abnormalities in blood cell morphology.

A rapid diagnostic test (RDT) and a blood smear examination are mostly used in tests for parasitic diseases such as malaria. In the case of the RDT, there is an advantage in which a convenient, prompt test is performed using a relatively low-cost diagnostic kit, but there is a problem in that a test result is quite inaccurate. Consequently, nowadays, a blood smear examination is recommended for a more accurate test.

A blood smear examination is a method of testing for a disease by injecting a patient's blood in a slide, smearing and staining the blood, and observing the stained blood using a microscope. Since a processes of smearing or staining blood and observing it with a microscope depends on manual work of a tester in a conventional blood smear examination, there is a problem in that it is difficult to smoothly carry out the test since a state of the smeared blood is not uniform or blood is erroneously stained due to an error of a reaction condition in a staining process when a tester is unskilled. Accordingly, it is actually difficult to apply a blood smear examination to a test for a disease in underdeveloped countries such as some countries in Africa which lack medical personnel.

SUMMARY OF THE INVENTION

An aspect of the present disclosure is to provide a gel-phase contact-type staining patch that comes into contact with a specimen to stain the specimen.

Another aspect of the present disclosure is to provide a contact-type staining patch that is manufactured in advance to be used any time.

Yet another aspect of the present disclosure is to provide a contact-type staining patch that can be used several times.

Still another aspect of the present disclosure is to provide a contact-type staining patch that can be conveniently used by omitting or simplifying steps such as preprocessing (fixing) or postprocessing (washing and drying) during a staining process.

Still another aspect of the present disclosure is to provide a contact-type staining supplementary patch that performs various actions to assist in staining during a staining process.

Still another aspect of the present disclosure is to provide a contact-type staining supplementary patch that provides a buffering solution to a specimen that has received a staining sample during a staining process.

Still another aspect of the present disclosure is to provide a contact-type staining supplementary patch that performs a specimen fixing function, a mordanting function, a decolorizing function, etc. during a staining process.

Aspects of the present disclosure are not limited to those mentioned above, and unmentioned aspects will be clearly understood by those of ordinary skill in the art to which the present disclosure pertains from the present specification and the accompanying drawings.

According to an aspect of the present disclosure, there is provided a contact-type staining patch including a staining solution that reacts with a specimen and a gel receptor provided as a gel matrix of a mesh structure in which a pore that accommodates the staining solution is formed and the mesh structure prevents the staining solution in the pore from leaking or degenerating, and having a contact surface that comes into contact with the specimen to transfer some of the staining solution to the specimen.

According to another aspect of the present disclosure, there is provided a contact-type staining patch including a gel receptor provided as a gel matrix of a mesh structure in which a pore is formed and in which any one surface is a contact surface that comes into contact with a specimen; and a staining solution accommodated in the pore and configured to include a staining sample that reacts with the specimen and a buffering solution having a predetermined pH value to form an optimal pH when a reaction occurs between the specimen and the staining sample, wherein the mesh structure inhibits a leakage to an outside or contamination of the staining solution and stores the staining solution in the gel receptor while maintaining the predetermined pH value of the staining solution, and, when the contact surface comes into contact with the specimen, allows some of the staining solution to move to the specimen and stain the specimen.

According to yet another aspect of the present disclosure, there is provided a contact-type staining patch including a staining solution that includes a first staining sample that stains a specimen and a second staining sample that stains the specimen and is different from the first staining sample; and a gel receptor provided as a gel matrix that forms a pore configured to accommodate the staining solution and store the staining solution accommodated in the pore, and configured to come into contact with the specimen to transfer the first staining sample and the second staining sample to the specimen.

According to still another aspect of the present disclosure, there is provided a method of staining a specimen using a contact-type staining patch that includes a staining solution configured to react with the specimen, and a gel receptor provided as a gel matrix of a mesh structure in which a pore that accommodates the staining solution is formed and the mesh structure prevents the staining solution in the pore from leaking or degenerating, and having a contact surface that comes into contact with the specimen to transfer some of the staining solution to the specimen, the method comprising: preparing the contact-type staining patch; contacting the specimen with the contact surface of the contact-type staining patch; and staining the specimen by the contact-type staining patch.

According to still another aspect of the present disclosure, there is provided a contact-type staining patch that directly comes into contact with a specimen to stain the specimen, the contact-type staining patch comprising: a gel receptor having a predetermined concentration of a gelable powder mixed with an aqueous solution; and a staining sample contained in the gel receptor and configured to move from the gel receptor to the specimen to stain the specimen when contact occurs between the gel receptor and the specimen.

According to still another aspect of the present disclosure, there is provided a method of manufacturing a contact-type staining patch provided with a gel receptor that accommodates a staining sample in a pore formed therein, prevents, by a mesh structure, the staining sample from leaking or being contaminated, and transfers the staining sample to the specimen to stain the specimen when in contact with the specimen, the method comprising: mixing an aqueous solution, a gelable powder, and the staining sample; boiling the mixture mixed in the mixing; and cooling the mixture to a gel phase.

According to still another aspect of the present disclosure, there is provided a method of manufacturing a contact-type staining patch provided with a gel receptor that accommodates a staining sample in a pore formed therein, prevents, by a mesh structure, the staining sample from leaking or being contaminated, and transfers the staining sample to the specimen to stain the specimen when in contact with the specimen, the method comprising: mixing a buffering solution that forms an optimal pH at the specimen when in contact with the specimen with a gelable powder; heating the mixture of the buffering solution and the gelable powder; and stirring and cooling the mixture to transition the mixture to a gel phase, wherein, during the transition, the staining sample in a form of a solution is administered into the mixture.

According to still another aspect of the present disclosure, there is provided a method of manufacturing a contact-type staining patch provided with a gel receptor that accommodates a staining sample in a pore formed therein, prevents, by a mesh structure, the staining sample from leaking or being contaminated, and transfers the staining sample to the specimen to stain the specimen when in contact with the specimen, the method comprising: mixing a buffering solution that forms an optimal pH at the specimen when in contact with the specimen with a gelable powder; heating the mixture of the buffering solution and the gelable powder; cooling the mixture to transition the mixture to a gel phase; and absorbing the staining sample into the gel phase substance.

According to still another aspect of the present disclosure, there is provided a contact-type buffering patch configured to come into contact with a stained specimen to form an optimal pH at the specimen, the contact-type buffering patch comprising: a buffering solution having a predetermined pH value related to an optimal pH of a staining sample; and a gel receptor configured to accommodate the buffering solution.

According to still another aspect of the present disclosure, there is provided a contact-type fixating patch configured to come into contact with a specimen placed on a slide to fix the specimen to the slide, the contact-type fixating patch comprising: a specimen fixating agent configured to fix the specimen onto the slide; and a gel receptor configured to accommodate the fixating agent.

According to still another aspect of the present disclosure, there is provided a contact-type decolorizing patch configured to come into contact with a stained specimen to decolorize the specimen, the contact-type decolorizing patch comprising: a decolorizing agent configured to remove a staining sample that has stained the specimen from the specimen to decolorize the specimen; and a gel receptor configured to accommodate the decolorizing agent.

According to still another aspect of the present disclosure, there is provided a contact-type mordanting patch configured to come into contact with a stained specimen to mordant the specimen, the contact-type mordanting patch comprising: a mordanting agent configured to react with a staining sample that has stained the specimen so the staining sample forms a color; and a gel receptor configured to accommodate the mordanting agent.

According to still another aspect of the present disclosure, there is provided a method of manufacturing a contact-type buffering patch that comes into contact with a stained specimen to form an optimal pH of a staining sample that has stained the specimen, the method comprising: mixing a buffering solution having a predetermined pH value related to the optimal pH of the staining sample; heating the mixture mixed in the mixing; and cooling the mixture to a gel phase.

According to still another aspect of the present disclosure, there is provided a staining method comprising: staining a specimen using a staining sample by contacting the specimen with a gel-phase staining patch that accommodates the staining sample; and forming an optimal pH of the staining sample at the specimen by contacting the specimen with a gel-phase buffering patch that accommodates a buffering solution having a predetermined pH value related to the optimal pH of the staining sample.

According to still another aspect of the present disclosure, there is provided a staining method using a dye that includes a first staining sample and a second staining sample, the staining method comprising: staining a specimen with the first staining sample by contacting the specimen with a gel-phase first staining patch that accommodates the first staining sample; staining the specimen with the second staining sample by contacting the specimen with a gel-phase second staining patch that accommodates the second staining sample; and creating an optimal pH of the dye at the specimen by contacting the specimen with a gel-phase buffering patch that accommodates a buffering solution having a predetermined pH value related to an optimal pH of the dye.

Solutions of the present disclosure are not limited to those mentioned above, and unmentioned solutions should be clearly understood by those of ordinary skill in the art to which the present disclosure pertains from the present specification and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee The above and other objects, features and advantages of the present invention will become more apparent to those of ordinary skill in the art by describing exemplary embodiments thereof in detail with reference to the accompanying drawings, in which:

FIG. 25 is a view illustrating a blood smearing process using the smearing unit of the test kit according to the embodiment of the present disclosure;

DETAILED DESCRIPTION OF EXEMPLARY EMBODIMENTS

Figure 1:
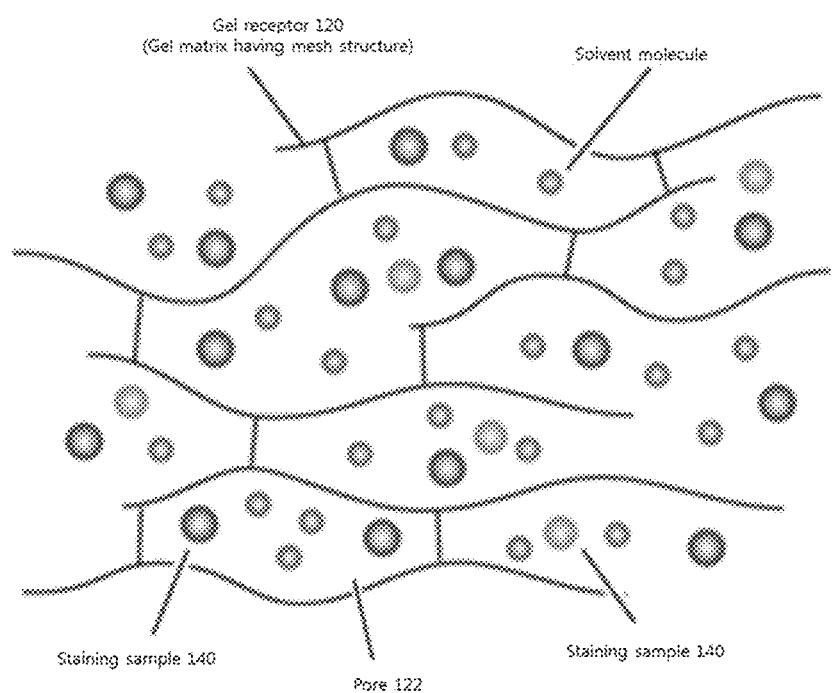
FIG. 1 is a cross-sectional view of a contact-type staining patch according to an embodiment of the present disclosure.

Since embodiments described herein are for clearly describing the spirit of the present disclosure to those of ordinary skill in the art to which the present disclosure pertains, the present disclosure is not limited to the embodiments described herein, and the scope of the present disclosure should be construed as including revised examples or modified examples not departing from the spirit of the present disclosure.

General terms currently being used as widely as possible have been selected as terms used herein in consideration of functions in the present disclosure, but the terms may be changed according to intentions and practices of those of ordinary skill in the art to which the present disclosure pertains or the advent of new technologies, etc. However, unlike the above, when a particular term is defined as a certain meaning and used, the meaning of the term will be separately described. Consequently, the terms used herein should be construed based on substantial meanings of the terms and content throughout the present specification instead of simply based on names of the terms.

The accompanying drawings herein are for easily describing the present disclosure. Since shapes illustrated in the drawings may have been exaggerated and displayed as needed to assist in understating the present disclosure, the present disclosure is not limited by the drawings.

When detailed description of a known configuration or function related to the present disclosure is deemed to blur the gist of the present disclosure in the present specification, the detailed description related thereto will be omitted as needed.

According to an aspect of the present disclosure, there is provided a contact-type staining patch including a staining solution that reacts with a specimen and a gel receptor provided as a gel matrix of a mesh structure in which a pore that accommodates the staining solution is formed and the mesh structure prevents the staining solution in the pore from leaking or degenerating, and having a contact surface that comes into contact with the specimen to transfer some of the staining solution to the specimen.

Herein, the staining solution includes a staining sample configured to react with the specimen and a solvent configured to create a reaction condition of the staining sample;

and the gel receptor uses the mesh structure to maintain a reaction condition of the staining solution.

Herein, in a process in which the staining solution is transferred to the specimen through the contact surface, the gel receptor inhibits excessive movement of the staining solution by using the mesh structure to prevent residue from remaining at the specimen.

Herein, the contact-type staining patch is a staining patch configured to assign a color to a specific component of the specimen, an antibody patch including an antibody that causes an antigen-antibody reaction with the specimen, or a DNA patch including a DNA probe that couples to a specific DNA sequence of the specimen.

Herein, the staining solution includes a detection inducing substance selected from a staining substance that directly stains the specimen, a precipitation/aggregation inducing substance that either precipitates or aggregates the specimen, a fluorescent substance that allows the specimen to form a fluorescent color, an isotope that allows the specimen to be detected with radiation, and an enzyme attached to the specimen which secretes a detectable substance.

Herein, the staining solution includes an attaching substance that is coupled to the detection inducing substance and reacts with a specific component of the specimen to be attached to the specimen; and the attaching substance includes an antibody that causes an antigen-antibody reaction with the specimen or a DNA probe that has a sequence complementary to a specific DNA sequence of the specimen.

Herein, the staining solution is provided in a liquid state; and the gel receptor is provided as hydrogel that inhibits a leakage of the staining solution in the liquid state to the outside.

According to another aspect of the present disclosure, there is provided a contact-type staining patch including a gel receptor provided as a gel matrix of a mesh structure in which a pore is formed and in which any one surface is a contact surface that comes into contact with a specimen; and a staining solution accommodated in the pore and configured to include a staining sample that reacts with the specimen and a buffering solution having a predetermined pH value to form an optimal pH when a reaction occurs between the specimen and the staining sample, wherein the mesh structure inhibits a leakage to an outside or contamination of the staining solution and stores the staining solution in the gel receptor while maintaining the predetermined pH value of the staining solution, and, when the contact surface comes into contact with the specimen, allows some of the staining solution to move to the specimen and stain the specimen.

Herein, the predetermined pH value is the optimal pH or a pH that has a difference of a pH compensation value from the optimal pH.

Herein, a size of the predetermined pH value is within a pH range of 0.1 to 0.4.

Herein, the pH compensation value is determined according to at least one of a hardness and porosity of the gel receptor, a density of the mesh structure, and a gel concentration of the gel receptor.

Herein, the pH compensation value increases as the gel receptor is harder, increases as the porosity is smaller, increases as the density is higher, and increases as the gel concentration increases.

According to yet another aspect of the present disclosure, there is provided a contact-type staining patch including a staining solution that includes a first staining sample that stains a specimen and a second staining sample that stains the specimen and is different from the first staining sample; and a gel receptor provided as a gel matrix that forms a pore configured to accommodate the staining solution and store the staining solution accommodated in the pore, and configured to come into contact with the specimen to transfer the first staining sample and the second staining sample to the specimen.

According to still another aspect of the present disclosure, there is provided a method of staining a specimen using a contact-type staining patch that includes a staining solution configured to react with the specimen, and a gel receptor provided as a gel matrix of a mesh structure in which a pore that accommodates the staining solution is formed and the mesh structure prevents the staining solution in the pore from leaking or degenerating, and having a contact surface that comes into contact with the specimen to transfer some of the staining solution to the specimen, the method comprising: preparing the contact-type staining patch; contacting the specimen with the contact surface of the contact-type staining patch; and staining the specimen by the contact-type staining patch.

Herein, in the staining, the gel receptor maintains the staining solution in a state in which a reaction condition of the specimen is satisfied.

Herein, the method further comprises, after the staining, omitting processes of washing and drying the specimen and observing the stained specimen.

According to still another aspect of the present disclosure, there is provided a contact-type staining patch that directly comes into contact with a specimen to stain the specimen, the contact-type staining patch comprising: a gel receptor having a predetermined concentration of a gelable powder mixed with an aqueous solution; and a staining sample contained in the gel receptor and configured to move from the gel receptor to the specimen to stain the specimen when contact occurs between the gel receptor and the specimen.

Herein, the gel receptor is hydrogel.

Herein, the powder is an agar or agarose powder.

Herein, the gel receptor is an agarose gel having a concentration of 1 to 4%.

Herein, the patch further comprises at least one of an antiseptic, an antibiotic, and an evaporation preventing agent, wherein the antiseptic, the antibiotic, and the evaporation preventing agent are accommodated in the pore.

Herein, the staining sample is a Romanowsky staining solution.

Herein, the aqueous solution is a buffering solution that forms an optimal pH at the specimen when in contact with the specimen.

Herein, the buffering solution has a pH range of 6.8 to 7.4.

According to still another aspect of the present disclosure, there is provided a method of manufacturing a contact-type staining patch provided with a gel receptor that accommodates a staining sample in a pore formed therein, prevents, by a mesh structure, the staining sample from leaking or being contaminated, and transfers the staining sample to the specimen to stain the specimen when in contact with the specimen, the method comprising: mixing an aqueous solution, a gelable powder, and the staining sample; boiling the mixture mixed in the mixing; and cooling the mixture to a gel phase.

Herein, the staining sample includes at least one of Giemsa powder, Wright powder, Giemsa-Wright powder, methylene blue, eosin, and Azure 11.

Herein, the aqueous solution is a buffering solution that forms an optimal pH at the specimen when in contact with the specimen.

Herein, the powder is an agar or agarose powder.

Herein, the gel phase has an agarose gel phase concentration of 1 to 4%.

According to still another aspect of the present disclosure, there is provided a method of manufacturing a contact-type staining patch provided with a gel receptor that accommodates a staining sample in a pore formed therein, prevents, by a mesh structure, the staining sample from leaking or being contaminated, and transfers the staining sample to the specimen to stain the specimen when in contact with the specimen, the method comprising: mixing a buffering solution that forms an optimal pH at the specimen when in contact with the specimen with a gelable powder; heating the mixture of the buffering solution and the gelable powder; and stirring and cooling the mixture to transition the mixture to a gel phase, wherein, during the transition, the staining sample in a form of a solution is administered into the mixture.

Herein, the heating is performed by baking using a microwave.

According to still another aspect of the present disclosure, there is provided a method of manufacturing a contact-type staining patch provided with a gel receptor that accommodates a staining sample in a pore formed therein, prevents, by a mesh structure, the staining sample from leaking or being contaminated, and transfers the staining sample to the specimen to stain the specimen when in contact with the specimen, the method comprising: mixing a buffering solution that forms an optimal pH at the specimen when in contact with the specimen with a gelable powder; heating the mixture of the buffering solution and the gelable powder; cooling the mixture to transition the mixture to a gel phase; and absorbing the staining sample into the gel phase substance.

Herein, in the absorbing, the gel phase substance is injected into a container that accommodates the staining sample.

According to still another aspect of the present disclosure, there is provided a contact-type buffering patch configured to come into contact with a stained specimen to form an optimal pH at the specimen, the contact-type buffering patch comprising: a buffering solution having a predetermined pH value related to an optimal pH of a staining sample; and a gel receptor configured to accommodate the buffering solution.

Herein, the gel receptor has a contact surface that comes into contact with the specimen, and, when the contact surface is in contact with the specimen, an optimal pH related to staining is created at the specimen to cause a reaction between the specimen and the staining sample.

Herein, the predetermined pH value is identical to an optimal pH value of the reaction.

Herein, the predetermined pH value is smaller than the optimal pH when the optimal pH is acidic and is larger than the optimal pH when the optimal pH is basic.

Herein, a difference between the predetermined pH value and the optimal pH is determined according to at least one of a hardness of the gel receptor, a porosity of the gel receptor, a gel concentration of the gel receptor, and a density of a mesh structure of the gel receptor.

Herein, the gel receptor is hydrogel.

Herein, the hydrogel is an agarose gel.

Herein, the gel receptor has an agarose concentration of 1 to 3%.

Herein, the gel receptor has a mesh structure in which a pore that accommodates the buffering solution therein is formed, and leakage to an outside or degeneration of the buffering solution is prevented by the mesh structure.

Herein, the gel receptor has a mesh structure in which a pore that accommodates the buffering solution therein is formed, and controls transfer of the buffering solution to the specimen to inhibit residue from remaining at the specimen when contact occurs between the specimen and the buffering solution.

Herein, the staining sample is a Romanowsky staining solution; and the buffering solution has a pH of 6.6 to 7.6.

According to still another aspect of the present disclosure, there is provided a contact-type fixating patch configured to come into contact with a specimen placed on a slide to fix the specimen to the slide, the contact-type fixating patch comprising: a specimen fixating agent configured to fix the specimen onto the slide; and a gel receptor configured to accommodate the fixating agent.

Herein, the fixating agent is alcohol.

Herein, the gel receptor is a non-hydrogel.

According to still another aspect of the present disclosure, there is provided a contact-type decolorizing patch configured to come into contact with a stained specimen to decolorize the specimen, the contact-type decolorizing patch comprising: a decolorizing agent configured to remove a staining sample that has stained the specimen from the specimen to decolorize the specimen; and a gel receptor configured to accommodate the decolorizing agent.

According to still another aspect of the present disclosure, there is provided a contact-type mordanting patch configured to come into contact with a stained specimen to mordant the specimen, the contact-type mordanting patch comprising: a mordanting agent configured to react with a staining sample that has stained the specimen so the staining sample forms a color; and a gel receptor configured to accommodate the mordanting agent.

According to still another aspect of the present disclosure, there is provided a method of manufacturing a contact-type buffering patch that comes into contact with a stained specimen to form an optimal pH of a staining sample that has stained the specimen, the method comprising: mixing a buffering solution having a predetermined pH value related to the optimal pH of the staining sample; heating the mixture mixed in the mixing; and cooling the mixture to a gel phase.

According to still another aspect of the present disclosure, there is provided a staining method comprising: staining a specimen using a staining sample by contacting the specimen with a gel-phase staining patch that accommodates the staining sample; and forming an optimal pH of the staining sample at the specimen by contacting the specimen with a gel-phase buffering patch that accommodates a buffering solution having a predetermined pH value related to the optimal pH of the staining sample.

According to still another aspect of the present disclosure, there is provided a staining method using a dye that includes a first staining sample and a second staining sample, the staining method comprising: staining a specimen with the first staining sample by contacting the specimen with a gel-phase first staining patch that accommodates the first staining sample; staining the specimen with the second staining sample by contacting the specimen with a gel-phase second staining patch that accommodates the second staining sample; and creating an optimal pH of the dye at the specimen by contacting the specimen with a gel-phase buffering patch that accommodates a buffering solution having a predetermined pH value related to an optimal pH of the dye.

Herein, the creating of the optimal pH of the dye at the specimen is performed at one or more times of a first time between the staining with the first staining sample and the staining with the second staining sample and a second time after the staining with the second staining sample.

Herein, in the creating of the optimal pH of the dye at the specimen, the buffering patch absorbs some of the first staining sample that reacts with the specimen first to induce a reaction between the second staining sample and the specimen.

1. Contact-Type Staining Patch 1.1 Gel-Phase Contact-Type Staining Patch

Hereinafter, a contact-type staining patch 100 according to an embodiment of the present disclosure will be described.

The contact-type staining patch 100 according to the embodiment of the present disclosure may come into contact with a specimen T and stain the specimen T.

For example, the contact-type staining patch 100 may be used in various ways such as for 1) techniques in which an object to be stained is directly reacted with a staining sample 140 to be stained including 1-1) a Giemsa staining technique or a Wright staining technique is accompanied by a blood smear examination including a peripheral blood smear examination used in an examination for malaria and 1-2) a simple staining technique, a Gram staining technique, or an AFB [Ziehl-Neelsen] technique accompanied by a bacteriological examination 2) a Papanicolaou smear test mostly used in cervical cancer examination, 3) a fluorescence staining technique such as 4,6-diamidino-2-phenylindole (DAPI), 4) techniques in which an antigen-antibody reaction is used and an object to be detected using an antibody coupled to an isotope, a florescent substance, an enzyme, etc. may indirectly form color by radiation detection, fluorescent color formation, and enzymes including 4-1) an immunohistochemistry technique which is a special staining technique used in screening for cancer or 4-2) an enzyme linked immunosorbent assay (ELISA) technique used in a human immunodeficiency virus (HIV) test, 5) a fluorescence in situ hybridization (FISH) technique in which, to check a specific DNA sequence, a fluorescent substance is coupled to a DNA probe complementary to a target sequence to detect the target sequence, and 6) a precipitation technique or a cohesion technique using an antigen-antibody reaction.

In the present disclosure, "staining" in the contact-type staining patch 100 is not to be construed as limited to directly staining an object to be detected from the specimen T, but should be construed as a term that comprehensively encompasses all methods in which a specific target substance may be detected and checked for in the specimen T such as a method in which an object to be detected can form a fluorescent color, a method in which radiation can be detected, a method in which the object to be detected can react and form color when injected in a specific substrate by an enzyme, and a method in which cohesion or precipitation is induced so that the object to be detected can be detected.

In other words, in the present disclosure, the contact-type staining patch 100 serves to make a substance to be tested be in a state detectable in the specimen T, and thus, according to the actual technical spirit thereof, a contact-type "detection inducing" patch would be a more clear expression. However, to assist in convenience of describing and understanding the present disclosure, the term, contact-type "staining" patch, will be used as a comprehensive meaning as needed.

Consequently, similar to above, it should be reasonable that the term, "stain" also be construed as having a wide meaning that encompasses all types of "detection inducing" that include inducing a fluorescent color formation, a color formation, radiation detection, precipitation, cohesion of an object to be detected, and inducing the object to be detected to be in other detectable states rather than being construed as having a narrow meaning of directly staining the object to be detected.

Meanwhile, along with the above, the specimen T refers to a substance that is an object to be tested, and it should be reasonable that the specimen T is construed as encompassing all biological samples that are subject to medical tests such as blood, cells, tissues, chromosomes, DNA, parasites, bacteria, etc.

Staining of the specimen T using the contact-type staining patch 100 may be performed as follows.

First, the contact-type staining patch 100 is provided in a gel phase, and the staining sample 140 is stored in a pore 122 therein. In this state, when the contact-type staining patch 100 is brought into contact with the specimen T, the staining sample 140 in the pore 122 inside the contact-type staining patch 100 passes through a mesh structure of a gel matrix, moves to the specimen T, and stains a substance to be stained.

1.1.1. Basic Composition of a Contact-Type Staining Patch

FIG. 1 is a cross-sectional view of the contact-type staining patch 100 according to an embodiment of the present disclosure.

Referring to FIG. 1, the contact-type staining patch 100 may include a gel receptor 120 and the staining sample 140.

The gel receptor 120 is provided with a gel-phase substance having a porous mesh structure that forms the pore 122 therein. The pore 122 of the gel receptor 120 may accommodate the staining sample 140.

The gel receptor 120 may be provided with various types of gel that form a gel matrix. For example, the gel receptor 120 may be gel formed of agarose. Here, agar may be used instead of agarose. When agar and agarose are compared to each other, the gel receptor 120 formed of agarose, which is a result of refining a polygalactose component in agar, has an advantage in terms of transparency or hardness, but a case in which agar is used may have an advantage in terms of cost when mass production is performed since a refining process and the like may be omitted.

Other than the above, a silicone gel, a silica gel, silicone rubber, polydimethylsiloxane (PDMS) known as a main component of a resin, a polymethylmethacrylate (PMMA) gel, and a gel using other various materials may be used as the gel receptor 120.

Hydrogel that can hold the staining sample 140 which is usually in the form of an aqueous solution may be used as the gel receptor 120, but, unlike the above, a non-hydrogel substance may also be used as needed.

The staining sample 140 is a substance that reacts with the specimen T to stain the specimen T. Here, the staining sample 140 should be construed as having a comprehensive meaning that encompasses all substances, not only staining reagents that directly stain the specimen T but also an antibody, a DNA probe, or the like to which a staining substance, a fluorescent substance, or the like is coupled, that react with a substance to be stained to make the substance to be stained detectable in examples of staining methods in which the contact-type staining patch 100 described above can be used.

For example, the staining sample 140 may include various types of staining solutions such as those used in Romanowsky staining techniques including acetocarmine, methylene blue, eosin, acid fuchsin, safranin, Janus Green B, hematoxylin, Giemsa solution, Wright solution, Wright- Giemsa solution, Leishman staining solution, Gram staining solution, carbol-fuchsin, and Ziehl-Neelsen solution.

As another example, the staining sample 140 may also include a DNA probe coupled to DAPI fluorochorme, a fluorescent substance, and an antibody coupled to an enzyme, a fluorescent substance, an isotope, etc. Of course, the staining sample 140 is not limited to the examples described above and may be any substance that reacts with a substance to be stained to make the substance to be stained detectable as mentioned above.

One staining sample 140 or two or more staining samples 140 may be mixed and stored in the pore 122.

For example, when attempting to perform a simple stain (a method of fixing bacteria and the like to a slide S and staining with one staining sample 140) using the contact-type staining patch 100, the one staining sample 140 may be stored in the pore 122. Here, methylene blue, crystal violet, safranin, etc. may be used as the staining sample 140. Similar to this, when attempting to use the contact-type staining patch 100 to detect only a specific sequence, one staining sample 140 in which a detection inducing substance such as a fluorescent substance is coupled to one type of DNA probe corresponding to the specific sequence may be used.

Unlike the example above, when attempting to perform a Giemsa stain using the contact-type staining patch 100, a composite sample formed of a heterogeneous staining substance including eosin, which stains cytoplasm red, and methylene blue, which stains a nucleus violet, may be used as the staining sample 140. That is, a first staining sample 140-1 which is eosin and a second staining sample 140-2 which is methylene blue may be mixed and stored in the pore 122.

Of course, a plurality of contact-type staining patches 100 each containing one staining sample 140 may also be used instead of mixing and storing a plurality of staining samples 140 in the pore 122 as described above in a staining technique in which a composite sample is used as the staining sample 140. For example, when attempting to perform a Giemsa stain, the staining samples 140 may also be separately stored in separate contact-type staining patches 100 like an eosin patch (a first contact-type staining patch 100-1 that stores eosin as the first staining sample 140-1) and a methylene blue patch (a second contact-type staining patch 100-2 that stores methylene blue as the second staining sample 140-2).

1.1.2 Buffering Solution of a Contact-Type Staining Patch

The staining sample 140 may be accommodated in the pore 122 of the gel receptor 120 in a form that is dissolved in a solvent as needed. Here, a buffering solution B that creates a reaction condition when a reaction occurs between the staining sample 140 and a substance to be stained may be used as the solvent.

The buffering solution B serves to create a reaction environment in which a reaction between an object to be stained and the staining sample 140 may occur during a staining reaction. For example, in a staining reaction such as a Giemsa stain, since basic methylene blue couples to a cell nucleus having a negative charge and stains the cell nucleus and acidic eosin stains a cytoplasm, pH concentrations are closely related to a staining result. Thus, creating proper pH concentrations may be extremely important for staining to be performed correctly. Consequently, in this case, the buffering solution B may be a pH buffering solution that maintains an optimal pH with respect to a reaction using the staining sample 140 of the contact-type staining patch 100.

Although it will also be described below in description related to a buffering patch, a solution with a pH concentration equal to an optimal pH of a staining reaction may be used as the buffering solution B.

Alternatively, a solution with a pH concentration slightly different from the optimal pH of the staining reaction may be used as the buffering solution B. Unlike a conventional staining process in which a large amount of the buffering solution B is sprayed to the specimen T which is stained in a buffer step to set an optimal pH, the buffering solution B in the contact-type staining patch 100 is contained in the gel receptor 120, and the optimal pH of a staining reaction is set during a process in which the contact-type staining patch 100 and the specimen T come into contact with each other. Here, when the buffering solution B is contained in the gel receptor 120, the buffering solution B may react with the staining sample 140 and the like and the pH of the buffering solution B may be slightly adjusted. To give a concrete example, in a case of the contact-type staining patch 100 that uses Giemsa dye as the staining sample 140, a pH of the buffering solution B rises slightly after manufacturing the contact-type staining patch 100 in comparison to the pH of the buffering solution B before manufacturing the contact-type staining patch 100. This is due to a factor caused by interactions among the buffering solution B, the staining sample 140, and the gel receptor 120 and a fact that an actually acting pH changes slightly when a buffering action is performed in a gel contact-type instead of in a conventional liquid spray type. Again, with respect to the contact-type staining patch 100 for a Giemsa stain, a pH of the buffering solution B contained in the contact-type staining patch 100 may be increased by approximately 0.1 to 0.4 in comparison to a pH of a raw material buffering solution B. When a desired optimal pH of a reaction is 6.8, a solution having a pH concentration of approximately 6.4 to 6.7 may be used as the buffering solution B. Setting an optimal pH of the contact-type staining patch 100 using a pH of the buffering solution B will be more clearly described in a buffering patch part below.

Specifically, when the contact-type staining patch 100 for a Giemsa stain manufactured using the buffering solution B having a pH of approximately 6.5 is brought into contact with the specimen T which is stained and the stained specimen T is observed, a staining result similar to that resulting from spraying the buffering solution B having a pH of approximately 6.6 to 6.9 onto the specimen T which is stained was actually observed.

In other words, an effective pH of the contact-type staining patch 100 manufactured using the buffering solution B having a specific pH value may be changed to be slightly different from a pH value of the buffering solution B itself. Here, an effective pH refers to a pH acting during a reaction between the specimen T and a patch and may be, for example, a pH created at the specimen T when the buffering solution B in a liquid phase is sprayed onto the specimen T.

Consequently, when manufacturing the contact-type staining patch 100, a pH of the buffering solution B has to be adjusted so that the effective pH value of the contact-type staining patch 100 is substantially equal to an optimal pH value of a staining technique.

That is, a pH value of the buffering solution B itself which will be used in a buffering patch may be set as a value compensated for by a pH compensation value in consideration of a pH biased due to interactions among a gel, a staining sample, and the buffering solution B in a gel matrix with respect to an optimal pH value that facilitates staining which may be defined in a conventional staining technique.

Here, the pH compensation value may be determined according to features of a gel, a type of a staining sample, an amount of a staining sample or a gel substance with respect to the buffering solution B, etc.

Here, with respect to features of a gel, a size (i.e., an absolute value) of the pH compensation value may be increased or decreased according to a concentration, a hardness, porosity, density of a mesh structure, etc. of a gel of the gel receptor 120. For example, a size of a pH compensation value may increase as a concentration of the gel of the gel receptor 120 increases, and a size of the pH compensation value may decrease as the concentration of the gel lowers. In addition, for example, when an agarose gel is used as the gel receptor 120, a size of the pH compensation value may increase as a concentration of agarose increases, and a size of the pH compensation value may decrease as the concentration of agarose lowers. In addition, a size of the pH compensation value may increase as the gel receptor 120 hardens, and a size of the pH compensation value may decrease as the gel receptor 120 softens. In addition, a size of the pH compensation value may decrease as porosity of the gel receptor 120 increases, and a size of the pH compensation value may increase as the porosity decreases. In addition, a size of the pH compensation value may increase as density of the mesh structure of the gel receptor 120 increases, and a size of the pH compensation value may decrease as the density lowers.

In addition, with respect to interactions of a staining substance, a larger pH shift may occur as an amount of the staining substance with respect to the buffering solution B increases, and whether it is shifted toward being acidic or basic may be determined according to a type of the staining substance. In a case of a Giemsa stain substance, a pH shift of approximately 0.1-0.4 toward being basic may occur with respect to a phosphate buffer saline (PBS) buffer. The pH shift may be larger as an amount of a staining substance with respect to the buffering solution increases, and a pH shift toward the basic direction may occur when a type of the staining substance changes.

In the contact-type staining patch 100 according to an embodiment of the present disclosure described above, the gel receptor 120 performs a function of storing the staining sample 140. Here, storing refers to 1) the gel receptor 120 preventing the staining sample 140 stored therein from leaking to the outside; and 2) preventing the staining sample 140 from being contaminated by the outside. The storing function is based on 1) a structural property of the gel matrix of the gel receptor 120; and 2) an electrochemical property of the gel receptor 120 and the staining sample 140.

The storing function based on the structural feature of the gel receptor 120 may be accomplished as the staining sample 140 accommodated in the pore 122 by the mesh structure of the gel receptor 120 is inhibited from moving up to a surface of the gel receptor 120. This will be described in detail as follows.

The gel receptor 120 may form the pore 122 in the mesh structure and accommodate the staining sample 140 inside the gel receptor 120. Here, the staining sample 140 has to move up to the surface of the gel receptor 120 from the pore 122 for the staining sample 140 inside the pore 122 to exit to the outside. In this process, since the staining sample 140 has to pass through the mesh structure, the staining sample 140 accommodated inside the pore 122 may be prevented from leaking to the outside. In other words, the mesh structure of the gel receptor 120 inhibits the staining sample 140 accommodated in the pore 122 from evaporating or leaking through the surface of the gel receptor 120. In addition, for the staining sample 140 to be contaminated, a contaminant from the outside has to pass through the surface of the gel receptor 120 and move up to the pore 122 inside the gel receptor 120. In this process, the mesh structure of the gel receptor 120 may inhibit foreign substances from being introduced into the gel receptor 120 and prevent the staining sample 140 inside the gel receptor 120 from being contaminated.

In addition, the storing function based on the electrochemical property of the gel receptor 120 may be accomplished by electrochemical reactivity between the gel receptor 120 and the staining sample 140. For example, when the staining sample 140 stored in the pore 122 of the gel receptor 120 is in a form of an aqueous solution, a hydrophilic gel may be prepared as the gel receptor 120 to inhibit the staining sample 140 from leaking to the outside from the gel receptor 120. In addition, according to the property of the gel receptor 120, since a substance with the opposite property cannot infiltrate into the gel receptor 120 from the outside (for example, a hydrophobic contaminant is inhibited from infiltrating into the hydrophilic gel receptor 120), the staining sample 140 stored in the gel receptor 120 can be prevented from being contaminated.

In addition, the storing function of the gel receptor 120 is not limited to simply preventing leakage or contamination of the staining sample 140. A reaction condition in staining is extremely important to smoothly stain blood in a blood smear examination. For example, when a proper pH concentration is not achieved, a reaction between the staining sample 140 and blood may not occur properly, erroneously stained blood may be observed with a microscope, and an error may occur in a test as a result.

With respect to the above, in the present disclosure, the staining sample 140 may be accommodated in the pore 122 of the gel receptor 120 while having a proper reaction condition and the gel receptor 120 may store the staining sample 140 while the reaction condition is maintained. For example, a Giemsa stain is performed under a pH of 7.2. For this, the staining sample 140 for the Giemsa stain may be stored in the form of an aqueous solution having a pH of 7.2 in the pore 122 of the gel receptor 120. Since leakage to the outside or contamination due to an external substance of the staining sample 140 or the aqueous solution is prevented by the mesh structure of the gel receptor 120, the staining sample 140 for the Giemsa stain may be stored in the form of an aqueous solution whose pH is maintained at 7.2 inside the gel receptor 120.

The contact-type staining patch 100 has an advantage of being able to protect the staining sample 140 for a long period while maintaining a desired reaction condition. This is a great advantage over a case in which a conventional staining technique is used in which a reaction condition needs to be set each time staining is conducted.

1.1.2 Additional Compositions of the Contact-Type Staining Patch

Meanwhile, the contact-type staining patch 100 may further include various additional compositions. Similar to the staining sample 140, the additional compositions may be accommodated in the pore 122 of the gel receptor 120 to be contained in the contact-type staining patch 100.

For example, an evaporation preventing agent may be included in the contact-type staining patch 100. The evaporation preventing agent may perform a role of preventing the staining sample 140 inside the gel receptor 120 from leaking to the outside by evaporation. Although the staining sample 140 stored in the pore 122 of the gel receptor 120 in a form of an aqueous solution and the like as described above is inhibited to some extent from leaking to the outside by a water-soluble property of the gel matrix structure or the gel receptor 120, the staining sample 140 may be stored for a long period while performance of the contact-type staining patch 100 is maintained by the evaporation preventing agent contained in the gel receptor 120. The evaporation preventing agent may have a weight ratio of 5% or less and may preferably have a weight ratio of 1% or less.

In another example, a degeneration preventing agent may be included in the contact-type staining patch 100. Like an antiseptic and an antibiotic that prevents proliferation of bacteria in the contact-type staining patch 100, the degeneration preventing agent performs a function of preventing the staining sample 140 inside the contact-type staining patch 100 from degenerating due to various causes. When the gel receptor 120 is exposed, bacteria or germs may proliferate therein, and performance of the contact-type staining patch 100 may be degraded as a result due to contamination of the staining sample 140. When the degeneration preventing agent is added to the contact-type staining patch 100, a shelf life of the contact-type staining patch 100 may be extended.

1.2. Staining Process Using the Contact-Type Staining Patch

Figure 2:
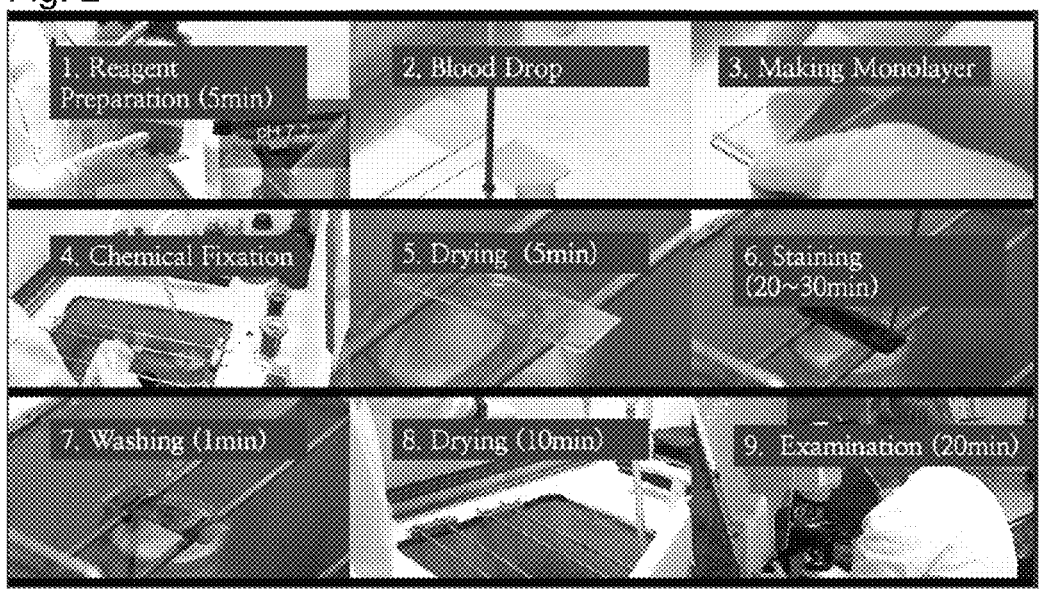
FIG. 2 is a view illustrating a conventional blood smear examination process.
Figure 3:
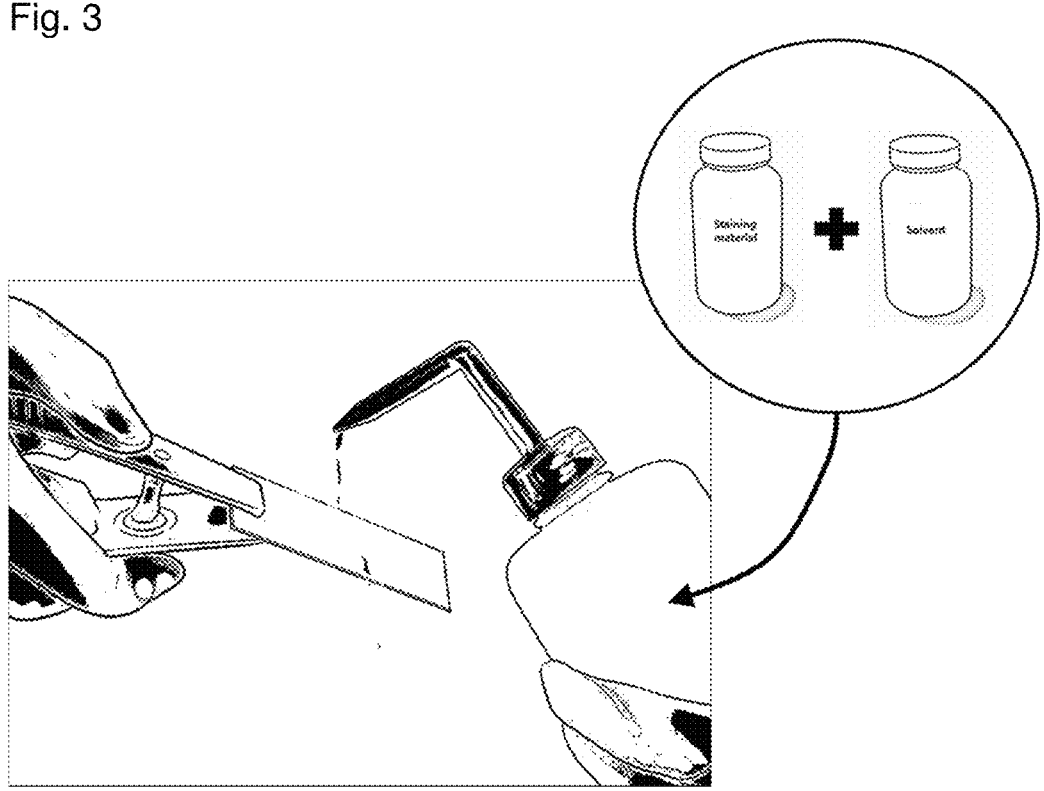
FIG. 3 is a view related to a process of preparing a staining solution and a staining process of the conventional blood smear examination process.

FIG. 2 is a view illustrating a conventional blood smear examination process, and FIG. 3 is a view related to a staining process of the conventional blood smear examination process.

Referring to FIG. 2, the conventional blood smear examination is conducted as follows. First, a reactant such as a staining solution is prepared. Next, blood is injected onto the slide S, and the blood is smeared. When the blood is smeared on the slide S, the blood is fixed and dried. The fixing of the smeared blood may be performed primarily using a chemical fixing means. When the smeared blood is fixed to the slide S, a staining solution is poured on it to stain the blood. Here, since the staining solution is poured onto the blood and thus a large amount of the staining solution is mixed with the blood, the mixture of the staining solution and the blood is washed and then dried again. Through this process, the stained blood on the slide S may be observed using a microscope and the like to conduct the blood smear examination.

Referring to FIG. 3, staining is performed in a form of spraying a staining solution onto the slide S on which blood is smeared in the conventional blood smear examination, and, for this, a staining solution has to be manufactured impromptu using a powdery staining sample 140. Consequently, manual work of a skilled person or separate equipment for mixing a proper ratio is required to set a ratio between the staining sample 140 and a solvent. Furthermore, when a staining solution was manufactured in advance, 1) the staining solution manufactured in advance may contact air and react; 2) a reaction between the solvent and the staining sample 140 may occur inside the staining solution; or 3) a reaction between heterogeneous staining samples 140 may occur when the staining solution is manufactured and used by mixing a plurality of staining samples 140. Accordingly, since the staining solution is contaminated or a proper reaction condition cannot be maintained, the staining solution can only be used for a few hours after manufacture.

With respect to this, since the contact-type staining patch 100 according to an embodiment of the present disclosure stores the staining sample 140 in the pore 122 therein that forms the mesh structure in the gel receptor 120 thereof while a desired reaction condition is maintained, the contact-type staining patch 100 can be manufactured in advance instead of manufacturing a staining solution at an examination site by mixing the staining sample 140 with a solvent, and the contact-type staining patch 100 can be used in examinations over a long period.

Figure 4:
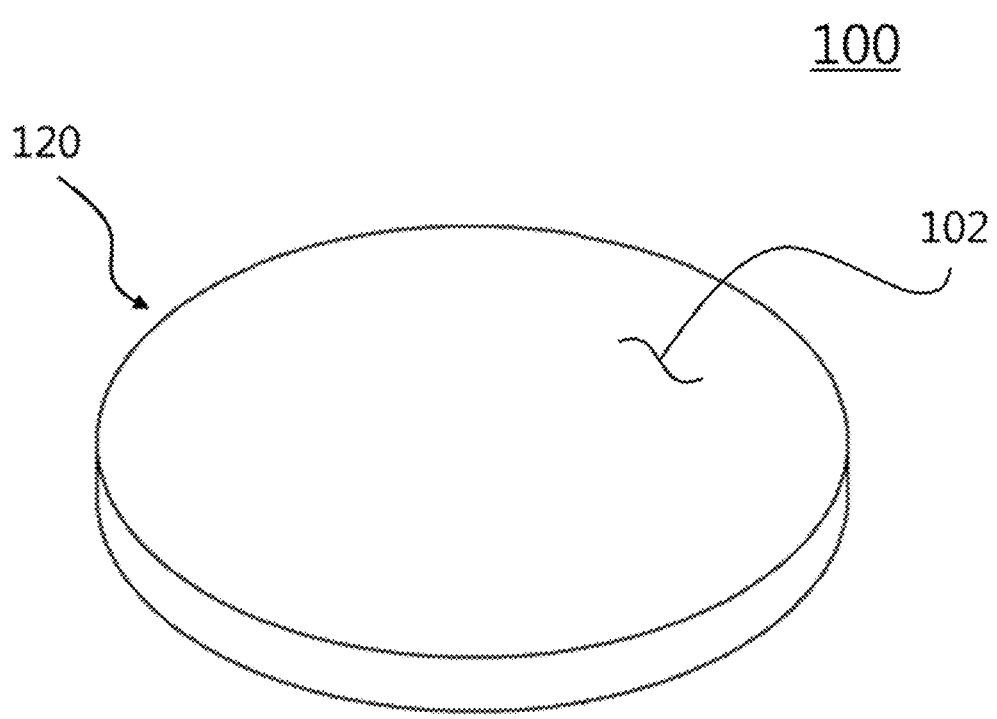
FIG. 4 is a perspective view of the contact-type staining patch according to an embodiment of the present disclosure.
Figure 5:
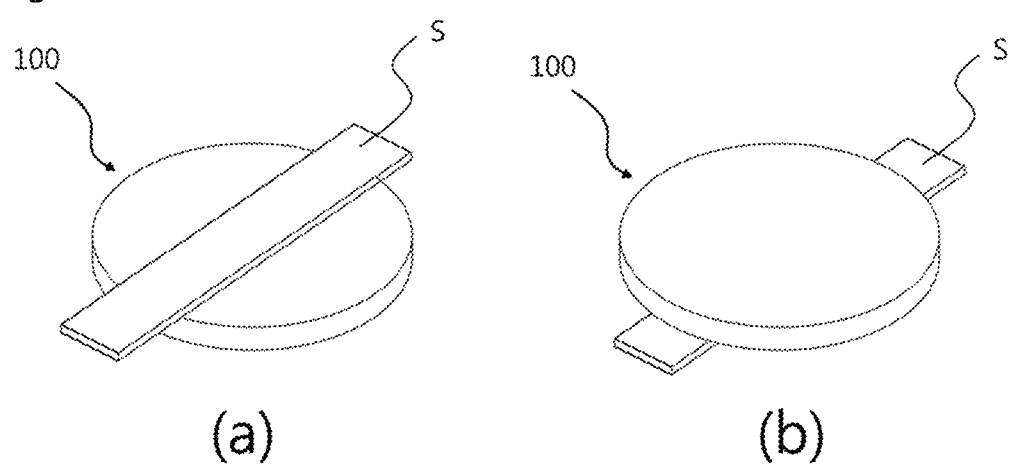
FIG. 5 is a view illustrating a contact state between the contact-type staining patch and a specimen slide according to an embodiment of the present disclosure.

FIG. 4 is a perspective view of the contact-type staining patch 100 according to an embodiment of the present disclosure, and FIG. 5 is a view illustrating a contact state between the contact-type staining patch 100 and the slide S according to an embodiment of the present disclosure.

Referring to FIG. 4, a shape of the contact-type staining patch 100 may be defined by a shape of the gel receptor 120 and may have a contact surface 102 for coming into contact with the specimen T formed on at least one surface thereof. Here, the contact surface 102 is a surface that directly comes into contact with the specimen T and may preferably be a plane to easily come into contact with the specimen T smeared on the slide S. For example, the contact-type staining patch 100 may be provided in the form of a column as illustrated in FIG. 4, and in such a cylindrical form, one of an upper surface and a lower surface of the column may be the contact surface 102.

With reference to FIG. 5, it can be seen that the contact-type staining patch 100 is brought into contact with the specimen T by mounting the slide S on which the specimen T is smeared on the upper surface of the contact-type staining patch 100 illustrated in FIG. 4 or, conversely, by mounting the contact-type staining patch 100 on the slide S on which the specimen T is smeared.

Meanwhile, the shape of the contact-type staining patch 100 is not limited to the shape illustrated in FIG. 4 and may also include a plurality of contact surfaces 102. For example, the contact-type staining patch 100 may be manufactured in a hexahedral shape, and one or a plurality of surfaces thereof may be used as the contact surfaces 102. In another example, the contact-type staining patch 100 may also be manufactured in a hemispherical shape in which a bottom surface thereof is the contact surface 102.

Figure 6:
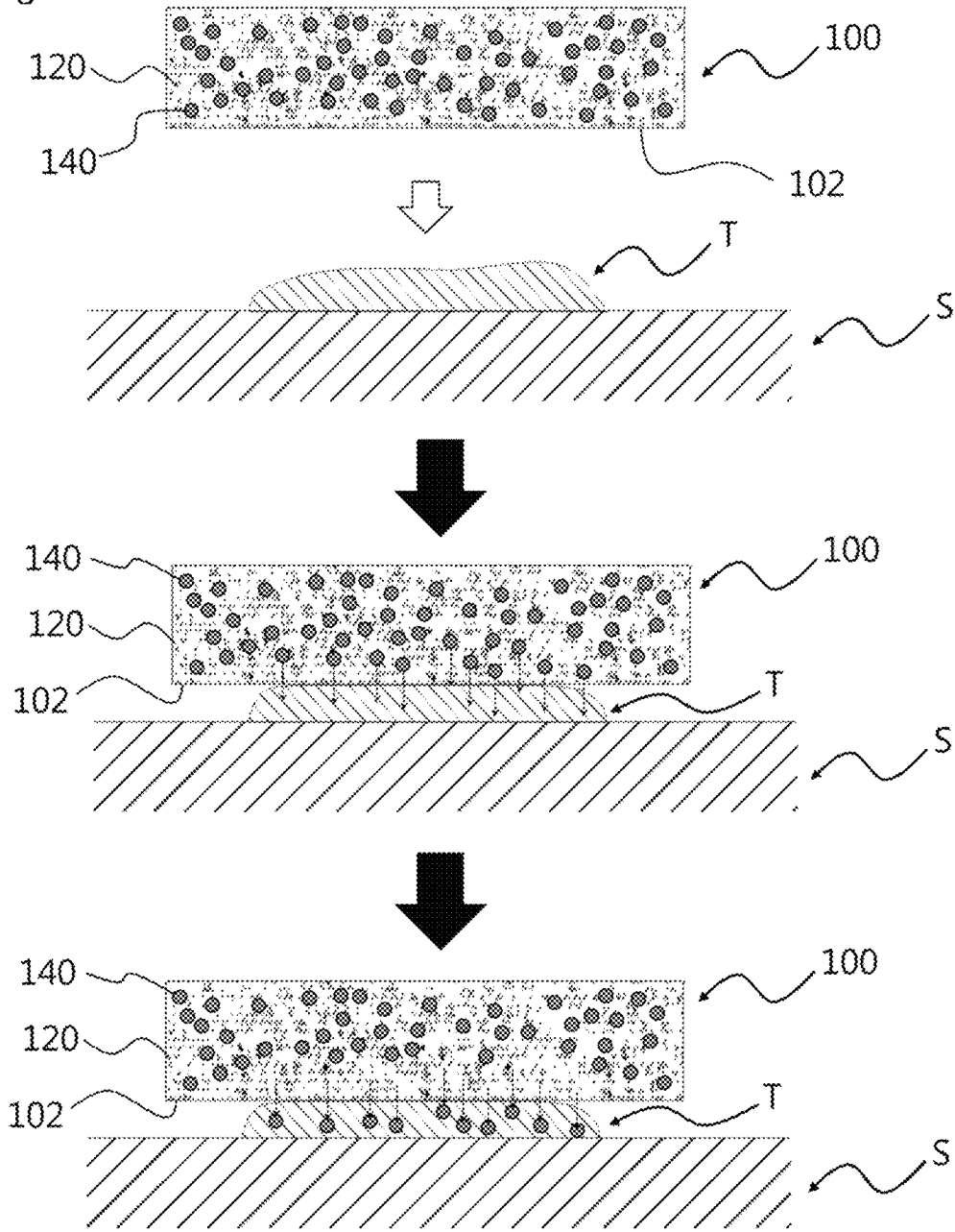
FIG. 6 is a view related to a staining process using the contact-type staining patch according to an embodiment of the present disclosure.

FIG. 6 is a view related to a staining process using the contact-type staining patch 100 according to an embodiment of the present disclosure.

Referring to FIG. 6, the contact-type staining patch 100 may come into contact with the specimen T smeared on the slide S. In other words, the contact surface 102 of the gel receptor 120 may directly come into contact with the specimen T. When the contact occurs, the staining sample 140 passes through the mesh structure and moves to the specimen T through the contact surface by an electrochemical action between a specific component in the specimen T that reacts with the specimen T or the staining sample 140 and the staining sample 140 stored inside the gel receptor 120, i.e., accommodated in the pore 122 therein. The staining sample 140 that has moved to the specimen T may react with the specimen T or the specific component in the specimen T and stain the specimen T.

Here, since the staining sample 140 is stored inside the gel receptor 120 while the reaction condition is maintained, staining can be smoothly performed even though the reaction condition is not separately adjusted.

Meanwhile, although the staining sample 140 passes through the mesh structure of the gel receptor 120 and moves to the specimen T by a force acting between the staining sample 140 and the specimen T or the specific component in the specimen T, since the movement is performed while being somewhat limited by the mesh structure, an excessively large amount of the staining sample 140 or the staining solution may be prevented from moving to the specimen T.

Here, the amount of the staining sample 140 or the staining solution moving to the specimen T may be controlled by adjusting a density of the mesh structure and a degree of liquidity, porosity, etc. of gel. That is, by properly adjusting a hardness of the gel, only a proper amount of the staining sample 140 may be transferred to the specimen T from the contact-type staining patch 100.

For example, when the contact-type staining patch 100 for a Giemsa stain is manufactured using an agarose gel for a peripheral blood smear examination, the concentration of agarose may preferably be 1 to 5%. When the concentration of agarose is higher than the range above, the movement of the staining sample 140 may be delayed and a sufficient amount of the staining sample 140 may not move to the blood, and thus a problem in which staining is not performed may occur. Conversely, when the concentration of agarose is lower than the range above, an excessive movement of the staining sample 140 may occur and a superfluous amount of the staining sample 140 may be transferred to the blood. Although staining can be smoothly performed when a superfluous amount of the staining sample 140 is transferred, there may be disadvantages in which the staining sample 140 is wasted and a residue remains on the blood such that washing and drying processes for removing the residue are required afterwards. Consequently, the concentration of agarose may preferably be 1.5 to 2.5%.

Meanwhile, referring again to FIG. 5, when the contact-type staining patch 100 is brought into contact with the specimen T, the contact-type staining patch 100 may either simply come into contact with the specimen T without any external pressure (only gravity acting during a simple vertical contact, but this may be viewed as having almost no pressure) or a predetermined pressure may be applied therebetween. This may be properly selected according to a hardness of the contact-type staining patch 100. For example, a sufficient amount of the staining sample 140 may be transferred to the specimen T with only a simple contact when the contact-type staining patch 100 is manufactured to be somewhat soft, and conversely, a predetermined pressure may need to be applied for a proper amount of the staining sample 140 to be transferred to the specimen T when the contact-type staining patch 100 is manufactured to be somewhat hard.

When the contact-type staining patch 100 that directly comes into contact with the specimen T to stain the specimen T is used, 1) staining can be performed under a correct reaction condition by only bringing the contact-type staining patch 100 into contact with the specimen T even though the reaction condition is not separately adjusted; 2) a waste of the staining sample 140 can be minimized; and 3) there is an advantage in which a staining process is simplified due to the omission of a preprocessing process such as fixing the specimen T before staining or a postprocessing process such as washing and drying after staining.

Referring again to FIGS. 2 and 3, the staining solution has to be manufactured impromptu for staining in the conventional blood smear examination, and there is a problem of an error in staining being likely due to a failure of setting a proper reaction condition due to a tester's mistake. Alternatively, even when separate equipment that properly mixes the staining sample 140 with a solvent is used to address the problem above, not only is an additional cost required for buying the mixing equipment, but an inconvenience of having to perform the mixing work each time the staining work is performed is also required such that there is a loss in terms of time and cost.

In contrast, the contact-type staining patch 100 according to an embodiment of the present disclosure stores the staining sample 140 maintained at a proper reaction condition therein and staining is correctly performed by only bringing the contact-type staining patch 100 into contact with the specimen T such that it is far more convenient and any one even someone who is not medical personnel can perform staining.

In addition, referring to FIGS. 2 and 3, staining is performed in the form of spraying a staining solution onto the slide S on which blood is smeared in the conventional blood smear examination, and there is a problem in which a large amount of the staining sample 140 is wasted in the above case. Not only is there great loss in terms of cost due to a difficulty of reusing the staining sample 140 that was sprayed once, there is a concern of negatively affecting the environment when the staining sample 140 is left alone such that a burden of managing the staining sample 140 is also added.

In contrast, the contact-type staining patch 100 according to an embodiment of the present disclosure transfers only a required amount of the staining sample 140 to blood by coming into contact with the specimen T while the staining sample 140 or a staining solution is stored therein such that the staining sample 140 can be saved, and recovery of the staining sample 140 after use is far more convenient since the staining sample 140 in a gel phase is brought into contact therewith instead of the staining sample 140 in a fluid form being sprayed thereto.

Furthermore, since the contact-type staining patch 100 can be stored for a long period, the contact-type staining patch 100 is not discarded after being used once and may also be used several times. Advantages in terms of cost and environmental protection become even clearer when the contact-type staining patch 100 is used several times.

In addition, referring to FIGS. 2 and 3, since staining is performed in the form of spraying a staining solution onto blood in the conventional blood smear examination, a preprocessing process of fixing blood on the slide S is required to prevent the blood from being swept away by the staining solution.

In contrast, the contact-type staining patch 100 according to the embodiment of the present disclosure transfers the staining sample 140 to blood through a simple contact such that, even when the specimen T remains on the slide S or some blood is swept away toward the contact-type staining patch 100 from the slide S in this process, only small amounts thereof are involved, and thus the specimen T may not have to be fixed on the slide S as needed. Of course, there may be cases in which fixating the specimen T is required to further optimize a test result. However, the benefit of fixating the specimen T is similar to the benefit generated due to the simplification of a test process such that the tester may select whether to fixate the specimen T with due consideration for the benefits.

In addition, referring to FIGS. 2 and 3, after the blood is stained, a sprayed staining solution remaining on the slide S has to be removed and thus postprocessing such as washing and drying is required in the conventional blood smear examination.

In contrast, in the contact-type staining patch 100 according to an embodiment of the present disclosure, the staining sample 140 or the staining solution is not excessively transferred to the slide S and thus residue is prevented from remaining on the slide S such that a washing process may be omitted, and due to the omission of the washing process, a drying process may also be omitted.

Particularly, there is a problem in which an erroneous staining result is brought about due to the washing process, e.g., an occurrence of decolorization when washing is performed for a long time, in the conventional blood smear examination. When the contact-type staining patch 100 according to an embodiment of the present disclosure is used, the washing process itself is unnecessary, and the erroneous staining itself due to the washing process can be prevented.

1.3. Method of Manufacturing a Contact-Type Staining Patch

Hereinafter, a method of manufacturing the contact-type staining patch 100 according to an embodiment of the present disclosure described above will be described.

An example of a method of manufacturing the contact-type staining patch 100 may include forming the gel receptor 120 and absorbing the staining sample 140 into the gel receptor 120.

First, the gel receptor 120 is formed using a gel raw material that serves as a gel formation substance, a gelable substance, etc. such as agarose powder and the like. For example, the gel receptor 120 may be manufactured when agarose powder and water are mixed at a proper ratio, and the mixture is heated and cooled. Here, boiling the mixture, baking the mixture using a microwave, or the like may be used as the heating. In addition, here, the cooling may include natural cooling or forced cooling, and a stirring process may be included in the cooling as needed.

Next, the staining sample 140 may be absorbed into the manufactured gel receptor 120. To absorb the staining sample into the gel receptor 120, a method in which the gel receptor 120 is dipped in a chamber, a container, or the like in which the staining sample 140 is accommodated for a predetermined amount of time and the gel receptor 120 is then taken out after the staining sample 140 is sufficiently absorbed thereinto may be used.

In another example, the method of manufacturing the contact-type staining patch 100 may include a method in which a gel raw material, an aqueous solution, and a staining sample are mixed to form a gel receptor. For example, the contact-type staining patch 100 may be manufactured by mixing agarose, an aqueous solution (or a buffering solution), and the staining sample 140 (which may be mixed with the buffering solution) at a proper ratio, and heating and cooling the mixture. Here, a heating and cooling means may be similar to the examples described above.

In yet another example, the method of manufacturing the contact-type staining patch 100 may include a method in which a gel raw material and a solution are mixed and heated and the staining sample 140 is then injected during a process of cooling the heated mixture. For example, after agarose and an aqueous solution are mixed at a proper ratio and heated, the staining sample 140 may be injected during a process of cooling the heated mixture.

1.4 Experimental Example of the Contact-Type Staining Patch

Hereinafter, an experimental example of the contact-type staining patch 100 according to an embodiment of the present disclosure described above will be described.

In this experimental example, the contact-type staining patch 100 according to an embodiment of the present disclosure is applied in a conventional Giemsa staining technique for an examination for malaria.

Meanwhile, since the Giemsa staining technique is merely described as a representative of Romanowsky staining techniques in various experimental examples which will be described below including this experimental example, embodiments are not limited to the Giemsa staining technique and may also be applied to other various Romanowsky staining techniques. In addition, a specimen staining technique performed using the contact-type staining patch 100 described herein has a simple procedure while effects of conventional Romanowsky staining techniques and other various staining techniques are maintained, and thus is expected to substitute therefor. A specimen staining technique will be referred to as "Noul stain" in a paper which will be written by the applicants in relation to the present disclosure.

The contact-type staining patch 100 was manufactured according to the following protocol.

1) After agarose, Giemsa powder, and the buffering solution B were mixed, the mixture was boiled and then cooled at room temperature. Agarose was used at 2% concentration, and the buffering solution B having a pH of 7.2 was used. Also, the mixture was heated to 100° C. or higher. Here, the concentration of agarose may be adjusted within a range of 1 to 3%. In addition, a pH concentration of the buffering solution B may be adjusted in a pH range of 6.4 to 7.6.

The contact-type staining patch 100 manufactured in this way was placed on blood smeared in a monolayer on the slide S for approximately five minutes, and then the staining result was observed using a 100× microscope. Blood collected from a mouse infected with plasmodium (a malaria-causing protozoan) was used.

Figure 7:
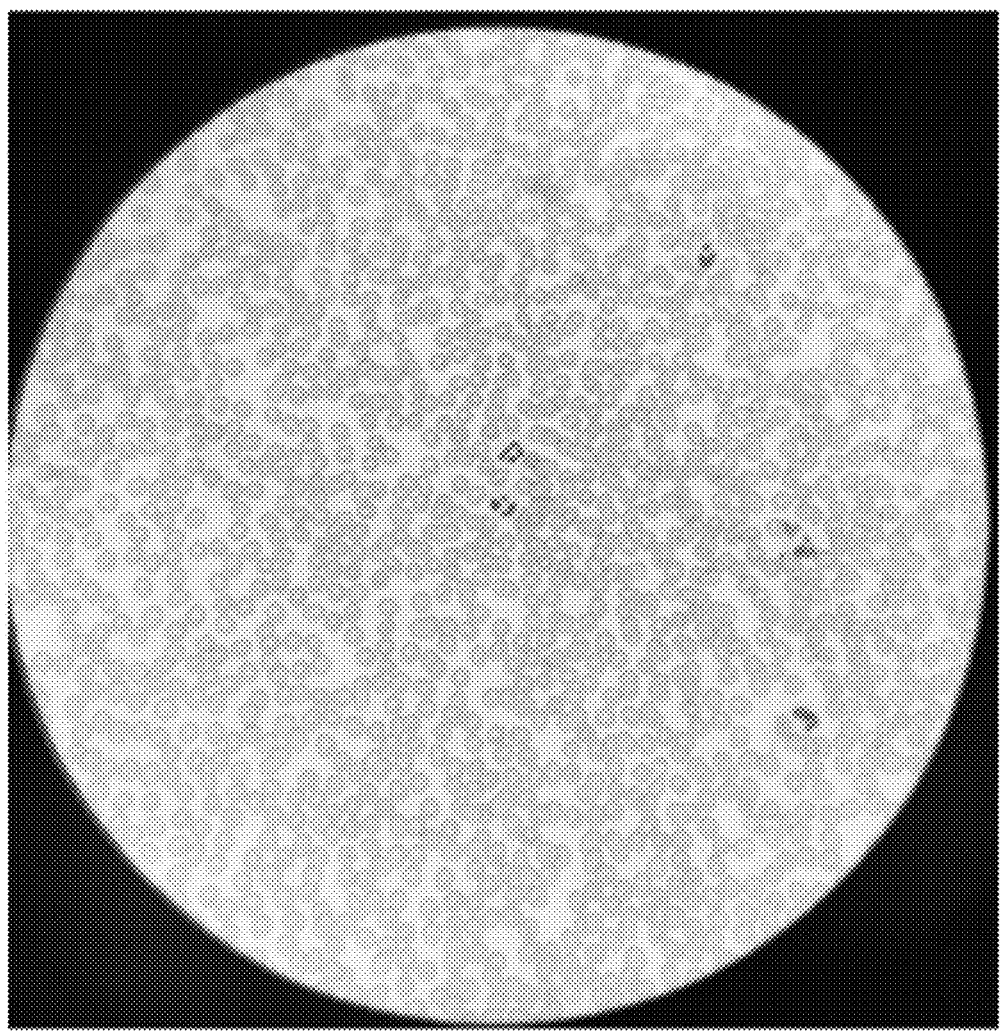
FIG. 7 is an image of a result of staining using a standard Giemsa stain process, i.e. a Giemsa staining technique, according to a conventional fluid spraying means.
Figure 8:
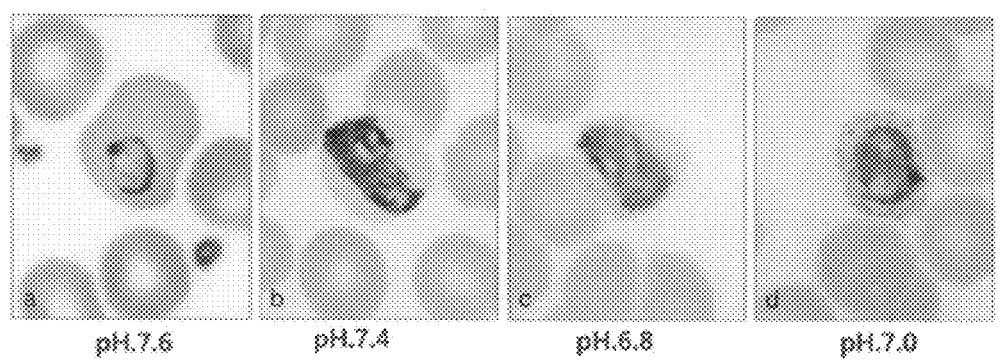
FIG. 8 shows images of results of staining using the Giemsa staining technique according to a standard Giemsa stain process for each pH concentration.
Figure 9:
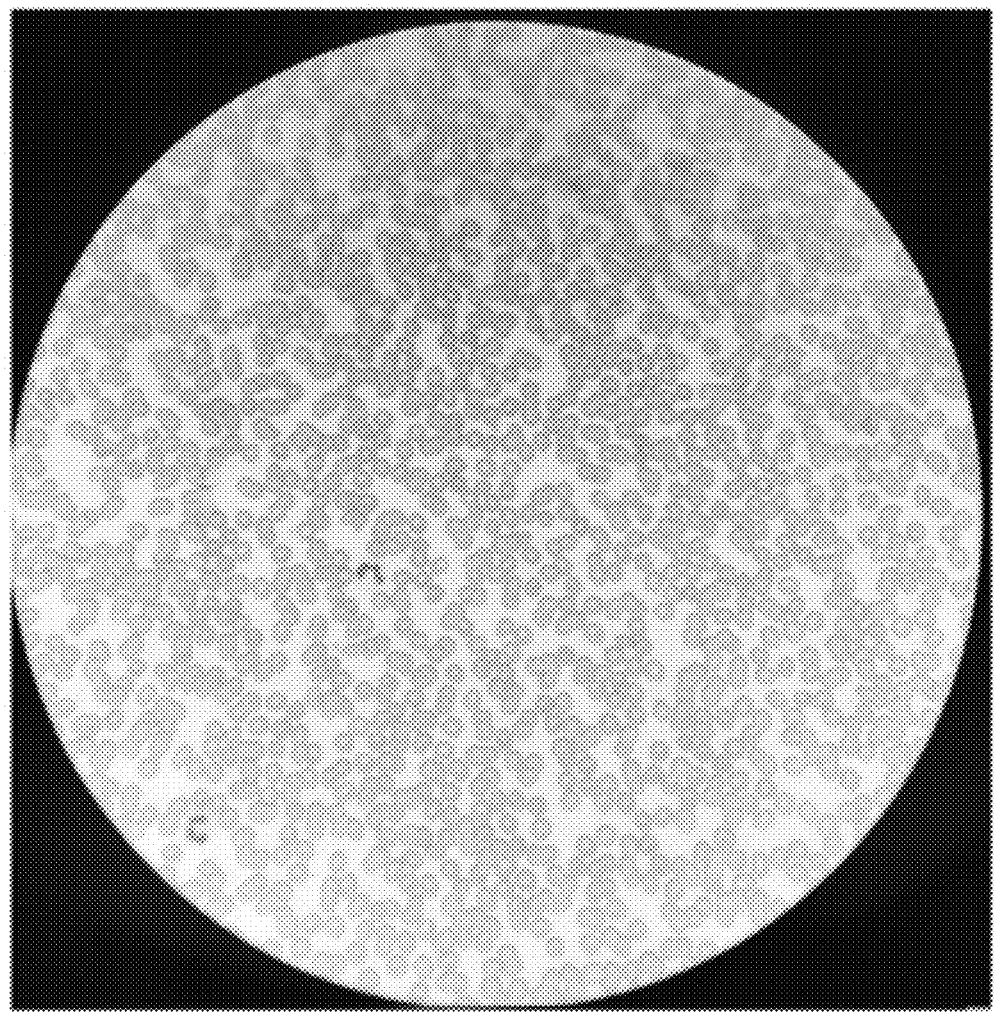
FIG. 9 is an image of a result of staining using the Giemsa staining technique in which the contact-type staining patch according to an embodiment of the present disclosure is applied.

FIG. 7 is an image of a result of staining using a standard Giemsa stain process, i.e. a Giemsa staining technique, according to a conventional fluid spraying means, FIG. 8 shows images of results of staining using the Giemsa staining technique according to a standard Giemsa stain process for each pH concentration, and FIG. 9 is an image of a result of staining using the Giemsa staining technique in which the contact-type staining patch 100 according to an embodiment of the present disclosure is applied.

FIG. 7 is a result of staining in which a proper pH concentration of the Giemsa stain is followed whereas FIG. 8 is a result of staining of a case in which a pH concentration deviates from a proper value during a staining process. Referring to FIG. 9, a result in which the contact-type staining patch 100 above is applied in the Giemsa staining technique shows a similar result with a correct staining result in which a proper pH concentration is followed. This suggests that staining using the contact-type staining patch 100 has been properly performed.

Particularly, a staining solution sprayed onto the slide S on which blood is smeared in the standard Giemsa stain process takes twenty to thirty minutes or more to stain. In contrast, when the contact-type staining patch 100 is used, the same result can be obtained within five minutes or less. Further, preparing a staining solution or washing, drying, etc. after staining is performed takes at least tens of minutes in the conventional standard process. In contrast, when the contact-type staining patch 100 is used, observation using a microscope is immediately possible after approximately tens of seconds of natural drying after staining is performed such that a time reduction effect is even greater.

Meanwhile, the contact-type staining patch 100 for an examination the same as that above may also be manufactured according to the following protocol.

2) After 0.4 g of agarose is mixed with 20 ml of a mixed solution of the buffering solution B having a pH of 7.2, the mixture is heated for thirty seconds using a microwave and cooled while being stirred. Then, 1 ml of a Giemsa modified solution is mixed therewith, and the mixture is further cooled and then hardened to a gel phase.

The contact-type staining patch 100 manufactured in this way was placed on blood smeared in a monolayer on the slide S for approximately five minutes, and then the staining result was observed using a 100× microscope. Blood collected from a mouse infected with plasmodium (a malaria-causing protozoan) was used.

Figure 10:
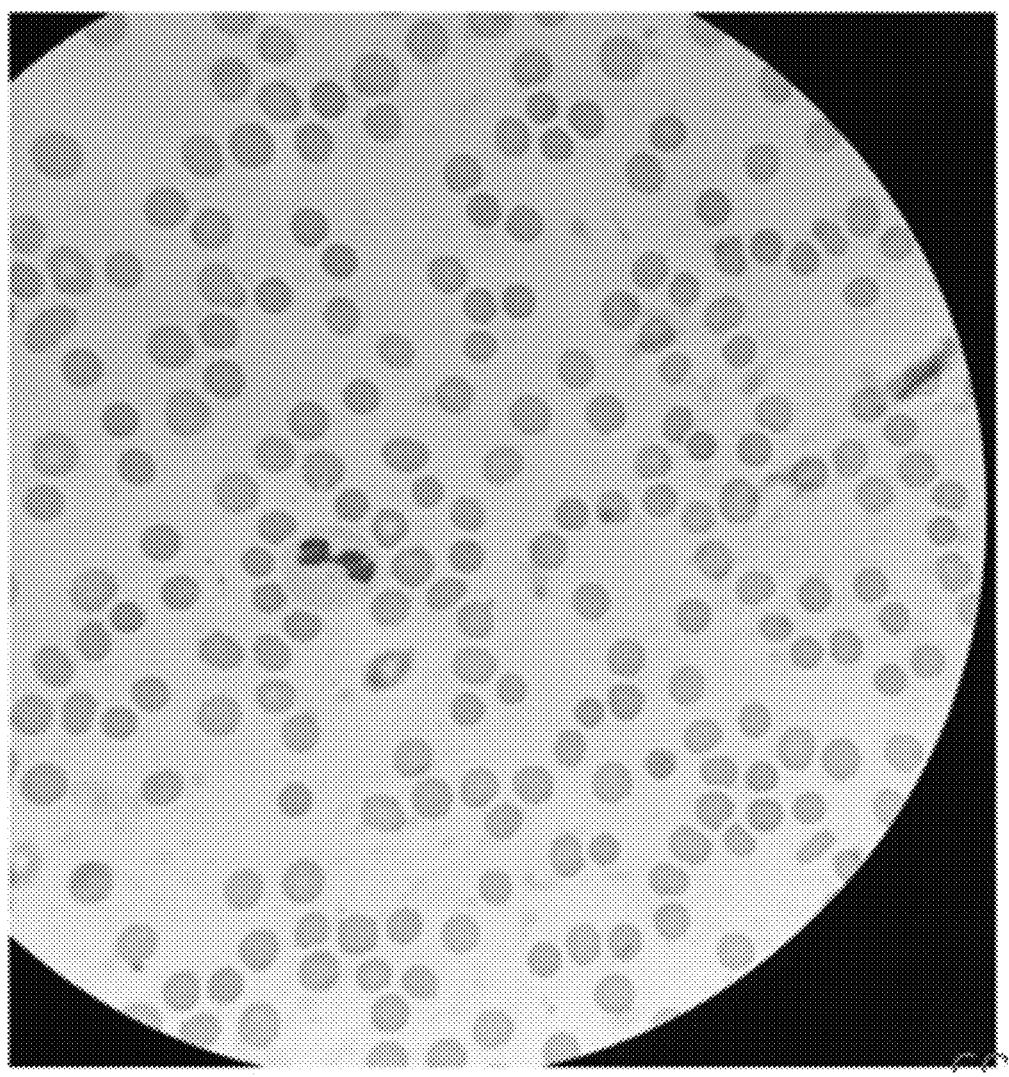
FIG. 10 is an image of another result of staining using the Giemsa staining technique in which the contact-type staining patch according to an embodiment of the present disclosure is applied.

FIG. 10 is an image of another result of staining using the Giemsa staining technique in which the contact-type staining patch 100 according to an embodiment of the present disclosure is applied. Referring to FIG. 10, a result in which the contact-type staining patch 100 manufactured using microwave baking described above is applied in the Giemsa staining technique also shows a similar result with a correct staining result in which a proper pH concentration is followed. Thus, this case also suggests that staining using the contact-type staining patch 100 has been properly performed.

In consideration of the staining results, the contact-type staining patch 100 according to an embodiment of the present disclosure is expected to have a more stable staining performance than a staining method that is performed according to the conventional standard process.

Although experimental examples in which the contact-type staining patch 100 is applied in the Giemsa staining technique has been described above, it should be self-evident that the contact-type staining patch 100 can also be applied to other different staining techniques.

Figure 11:
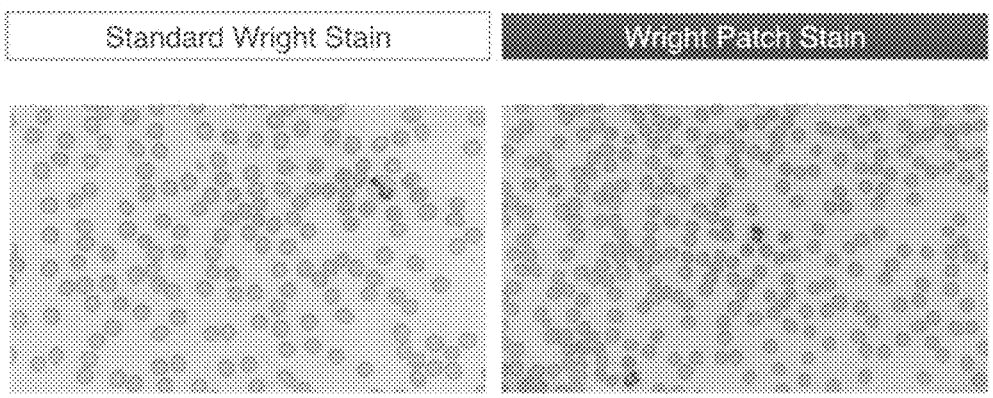
FIG. 11 is a view illustrating results according to a standard staining technique and a staining technique in which the contact-type staining patch is applied with respect to a Wright staining technique.

FIG. 11 is a view illustrating results according to a standard staining technique and a staining technique in which the contact-type staining patch 100 is applied with respect to a Wright staining technique.

For the contact-type staining patch 100 for the Wright stain, a gel-phase contact-type staining patch 100 was manufactured using a staining solution in which the buffering solution B having a pH of 6.8 was mixed with the Wright staining sample 140 and agarose. FIG. 11 shows a result of observation using a 400× microscope after the contact-type staining patch 100 was placed on the specimen T for approximately five minutes. As illustrated in FIG. 11, in the case of the Wright staining technique, it was also confirmed that a result almost the same as that according to the standard process was acquired.

Figure 12:
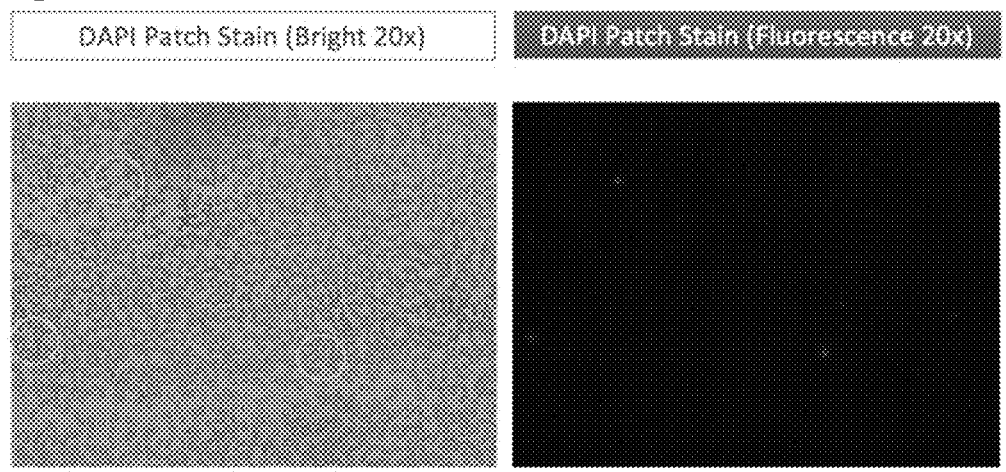
FIG. 12 is a view illustrating a result according to a staining technique in which the contact-type staining patch is applied with respect to a 4,6-diamidino-2-phenylindole (DAPI) staining technique.

FIG. 12 is a view illustrating a result according to a staining technique in which the contact-type staining patch 100 is applied with respect to a DAPI staining technique.

For the contact-type staining patch 100 for a DAPI stain, a gel-phase contact-type staining patch 100 was manufactured using 0.4 g of agarose, 20 ml of PBS, and 20 μl of DAPI. FIG. 12 shows results of observations which each used a Bright 20× and a Fluorescence 20× after the contact-type staining patch 100 was placed on the specimen T for approximately five minutes. As illustrated in FIG. 12, in the case of the DAPI staining technique, a stable fluorescent color formation was also confirmed as a result thereof.

In consideration of the staining results, the contact-type staining patch 100 according to an embodiment of the present disclosure is expected to simplify most of the standard processes of staining techniques that are conventionally performed as well as substitute therefor by guaranteeing a stable staining performance.

1.5. Utilization of the Contact-Type Staining Patch

In consideration of the above, representative examples of utilizing the contact-type staining patch 100 are as follows.

1.5.1 Staining Patch

In a conventional staining technique used in hematology, a liquid-phase staining solution was sprayed onto blood cells or tissue. However, with this method, residue remains on the specimen T, and it was difficult to control washing and drying processes, which are essential for removing the residue, to be regular. In addition, since a result sensitively changes according to a method of manufacture, a manufacture period, a change in a pH concentration of a buffer, etc. of staining reagents which are used, it was difficult to gain a stable staining result. Furthermore, the conventional standard processes required various types of equipment and, due to a great complexity of a protocol using the equipment, it was extremely difficult for an unskilled person to carry out the protocol.

A staining patch is an innovative improvement of the conventional staining technique and basically refers to a gel-phase receptor that holds the staining sample 140 in a hydrogel state. The staining patch may be manufactured by properly combining staining powder, hydrogel, the buffering solution B, a stabilizer, water, etc. as needed and enables a simple protocol in which staining is completed by the manufactured staining patch being brought into contact with and separated from blood cells or tissue for a relatively short amount of time.

The method has advantages in that washing and drying processes can be omitted from an overall staining process, an amount of time for staining itself is short, there is no residue such as a stain remaining on the specimen T, the use of samples can be minimized, and results are regular and stable compared to the conventional method.

As a result, the staining patch creates a reaction condition (or an environmental condition) in a staining process while holding water such that a chemical reaction is induced between the staining sample 140 and a substance to be reacted with while the water and other buffer substance are maintained as they are in the hydrogel, thereby not requiring the washing and drying processes.

Representative examples of the staining patch may include Romanowsky staining patches, such as a Giemsa patch and a Wright patch, and a Papanicolaou staining patch.

1.5.2. Antibody Patch

In performing immunohistochemistry or an enzyme linked immunosorbent assay (ELISA), an antibody patch is a patch capable of being delivered in a hydrogel state instead of a conventional liquid state in order to deliver an antibody or an antibody to which reporters such as a fluorescent substance are coupled.

Similar to the staining patch, the antibody patch is brought into contact with blood or a tissue for a predetermined amount of time. By this contact, antibodies stored inside a gel exit the antibody patch according to an antigen-antibody reaction, and the reaction ends.

When the antibody patch is used, a result may be obtained more promptly than the conventional means, washing and drying processes can be omitted, and background noise can be minimized.

1.5.3. DNA Patch

In performing the FISH test and the like, a DNA patch is a patch which delivers a DNA probe to which a fluorescent substance reporter is coupled, and is a patch that is delivered in a hydrogel state instead of a conventional liquid state.

Similar to the staining patch, the DNA patch is brought into contact with the specimen T such as blood, a tissue, or the like for a predetermined amount of time and then detached therefrom. By this contact, DNA probes exit the patch for hybridization, and the reaction ends.

Also in a DNA test, when the DNA patch is used, a more prompt and accurate result can be obtained compared to the conventional method, and washing and drying processes can be omitted.

Various examples of utilizing the contact-type staining patch 100 have been described above. However, fields in which the contact-type staining patch 100 can be utilized are not limited to those described above, and the contact-type staining patch 100 may be utilized in other various types of staining (a "wide meaning" defined herein which is inducing detection when a specimen is tested). Here, the staining sample 140 may be properly selected according to a field in which the contact-type staining patch 100 is utilized. For example, a staining substance may be used as the staining sample 140 in a case of a staining patch; an antibody may be used as the staining sample 140 in a case of an antibody patch; and a DNA probe may be used as the staining sample 140 in a case of a DNA patch.

2. Contact-Type Staining Supplementary Patch 100

The contact-type staining patch 100 that contains the staining sample 140 reacting with a substance to be reacted with of the specimen T has been described above. Hereinafter, a contact-type staining supplementary patch 100' according to an embodiment of the present disclosure that performs other processes performed throughout a staining process, e.g., fixing or buffering, decolorizing, mordanting, washing, etc. of the specimen T. will be described.

2.1. Examples of the Contact-Type Staining Supplementary Patch

A configuration of the contact-type staining supplementary patch 100' is basically substantially the same as that of the contact-type staining patch 100. Specifically, like the contact-type staining patch 100, the contact-type staining supplementary patch 100' includes the gel receptor 120 and may include a staining enhancing agent 160 instead of the staining sample 140.

The staining enhancing agent 160 may be selected according to a field in which the contact-type staining supplementary patch 100' is used.

2.1.1. Fixing Patch

For example, when being used to fix the specimen T, the staining enhancing agent 160 may be a specimen fixing agent such as alcohol (ethanol, methanol, or the like) that fixes the specimen T onto the slide S and the like.

2.1.2. Decolorizing Patch and Mordanting Patch

In another example, when the staining enhancing agent 160 is used for decolorizing or mordanting, a decolorizing agent or a mordanting agent may be used as the staining enhancing agent 160. In a Gram staining technique, after both Gram-positive bacteria and Gram-negative bacteria are stained using crystal violet as a main staining agent, the main staining agent is fixed to the Gram-positive bacteria using iodine as the mordanting agent, the main staining agent not fixed to the Gram-negative bacteria is then peeled off from the Gram-negative bacteria using a decolorizing agent such as alcohol (ethanol, methanol, etc.), and the decolorized Gram-negative bacteria is stained using safranin as a contrast staining agent such that the Gram-positive bacteria are stained by the main staining agent and the Gram-negative bacteria are stained by the contrast staining agent, and thus the two exhibit colors different from each other as a result. In this process, when actual staining is constituted only of the main staining agent and the contrast staining agent, the mordanting agent and the decolorizing agent do not perform staining itself but perform roles of assisting in staining. In the Gram staining technique, a main staining patch that uses crystal violet (a main staining agent) as the staining sample 140 and a contrast staining patch that uses safranin 0 (a contrast staining agent) as the staining sample 140 are prepared as the contact-type staining patch 100 according to an embodiment of the present disclosure, and a mordanting patch that contains iodine (a mordanting agent) as the staining enhancing agent 160 and a decolorizing patch that contains alcohol (a decolorizing agent) as the staining enhancing agent 160 are prepared as the contact-type staining supplementary patch 100' according to an embodiment of the present disclosure such that the Gram staining technique can be performed by bringing the main staining patch, the mordanting patch, the decolorizing patch, and the contrast staining patch into contact with the specimen T in that order.

When the contact-type staining supplementary patch 100' such as the fixing patch and the decolorizing patch is manufactured using the fixing agent or the decolorizing agent described above, a non-hydrogel may be mainly used for a material of the gel receptor 120 (of course, hydrogel may also be used according to circumstances). Alcohol with a high concentration (e.g., 99% or higher) may have to be used as the fixing agent to fix the specimen T on the slide S. Here, when hydrogel is used, the concentration of alcohol may be lowered due to an interaction between the gel receptor 120 and the alcohol, and accordingly, a fixing action may be degraded. In contrast, when the gel receptor 120 is a non-hydrogel, the concentration of alcohol can be maintained relatively well in the above case, and thus fixing performance or decolorizing performance can be improved. A PDMS gel, a PMMA gel, a silicone gel, or the like may be used as the non-hydrogel.

In addition, the fixing patch or the decolorizing patch may also be replaced with a fixing agent or a decolorizing agent that are a result of solidifying the gel receptor 120. For example, solidified-methanol itself may also be used as the fixing patch or the decolorizing patch.

2.1.3. Buffering Patch

In yet another example, there may be a buffering patch that uses the buffering solution B as the staining enhancing agent 160. The buffering patch may be a patch that creates a reaction condition (an environmental condition) for staining at the specimen T by coming into contact with the specimen T before, after, or both before and after the staining of the specimen T. In the case of the Giemsa stain, the buffering patch may be provided in a form in which the buffering solution B having a pH proper for the Giemsa stain is accommodated in the gel receptor 120.

A pH of the buffering solution B to be contained in the buffering patch may be substantially the same as a pH according to the reaction condition, i.e., an optimal pH.

Alternatively, unlike the above, the pH of the buffering solution B may be somewhat different from the optimal pH for a reaction.

When staining is performed, creating a proper staining environment, in particular, creating a proper pH, may be an important factor for properly performing staining. Generally, in a buffering step of the conventional staining procedure, a pH condition is set by spraying or spilling the buffering solution B having an optimal pH onto a specimen that is stained, being stained, or will be stained. In contrast, in a buffering step using the contact-type staining supplementary patch 100', a pH condition is created at a specimen by bringing the buffering patch into contact with the specimen T. Consequently, the contact-type staining supplementary patch 100' causes a buffering action in the specimen T according to a mechanism different from a conventional means in which a buffering solution in a liquid phase is brought into contact with a specimen.

Specifically, when a buffering patch manufactured using the buffering solution B that has an approximate pH of 6.5 is brought into contact with the specimen T that is stained and the stained specimen T is observed, a staining result similar to a result of spraying the buffering solution B having an approximate pH of 7.2 to 7.4 onto the specimen T that is stained is actually observed.

In consideration of the point above, it can be recognized that a pH created at the specimen T when the buffering solution B is provided to the specimen T while being contained in the gel receptor 120 is somewhat more biased toward a neutral pH than a pH created when the buffering solution B is directly sprayed onto the specimen T in a liquid phase. This is because, when the buffering solution B is directly provided using the buffering patch, an acid-base interaction that occurs between the buffering solution B and the specimen T occurs through the mesh structure of the gel matrix and thus may be somewhat delayed than an acid-base interaction between the buffering solution B sprayed in a liquid phase and the specimen.

In other words, an effective pH of the buffering patch manufactured using the buffering solution B having a specific pH value is somewhat more biased toward a neutral pH than a pH value of the buffering solution B itself. Here, the effective pH refers to a pH acting at the specimen T and may be, for example, a pH created at the specimen T when the buffering solution B in a liquid phase is sprayed onto the specimen.

Consequently, when the buffering patch is being manufactured, a pH of the buffering solution B has to be adjusted so that an effective pH value of the buffering patch is substantially the same as an optimal pH value of a staining technique in which the buffering patch will be used for buffering.

That is, a pH value of the buffering solution B itself that will be used in the buffering patch may be set as a value compensated for by a pH compensation value in consideration of an extent to which an acid-base interaction is hindered by the gel matrix with respect to an optimal pH value which facilitates staining that may be defined in a conventional staining technique.

Here, the pH compensation value may be a negative value when the optimal pH is acidic. For example, the pH compensation value may be −0.3 when the optimal pH is 6.8, and accordingly, a pH value of the buffering solution B used when the buffering patch is manufactured may be a pH of 6.5 for the effective pH of 6.8.

In addition, here, the pH compensation value may be a positive value when the optimal pH is basic. For example, the pH compensation value may be +0.2 when the optimal pH is 7.4, and accordingly, a pH value of the buffering solution B used when the buffering patch is manufactured may be a pH of 7.6 for the effective pH of 7.4.

A size (i.e., an absolute value) of the pH compensation value may be increased or decreased according to a concentration, a hardness, porosity, a density of a mesh structure, etc. of the gel of the gel receptor 120. The size of a pH compensation value may increase as a concentration of the gel of the gel receptor 120 increases, and the size of the pH compensation value may decrease as the concentration of the gel lowers. For example, when agarose gel is used as the gel receptor 120, the size of the pH compensation value may increase as a concentration of agarose increases, and the size of the pH compensation value may decrease as a concentration of agarose lowers.

In addition, the size of the pH compensation value may increase as the gel receptor 120 hardens, and the size of the pH compensation value may decrease as the gel receptor 120 softens.

In addition, the size of the pH compensation value may decrease as the porosity of the gel receptor 120 increases, and the size of the pH compensation value may increase as the porosity decreases.

In addition, the size of the pH compensation value may increase as the density of the mesh structure of the gel receptor 120 increases, and the size of the pH compensation value may decrease as the density lowers.

A pH shift phenomenon of the buffering patch is caused by a cause different from a case in which a pH of the buffering solution B is shifted when the staining sample 140 is mixed with the buffering solution B in the contact-type staining patch 100. That is, although pH shifting in the buffering patch occurs due to a cause described just above, pH shifting in the contact-type staining patch 100 may occur due to a complex cause that includes the cause described just above and a cause according to a part of description related to the buffering solution B of the contact-type staining patch 100.

Meanwhile, the above description on the pH compensation of the buffering solution B is not applied only to the buffering solution B included in the buffering patch but may be generally applied to the contact-type staining patch 100 or the contact-type staining supplementary patch 100' that has the buffering solution B. For example, even when the staining sample 140 included in the contact-type staining patch 100 is in a form of a solution in which a staining powder is mixed with the buffering solution B, a pH value that results from adding or subtracting a pH compensation value to or from an optimal pH may be set as a pH value of the buffering solution B instead of making the pH value of the buffering solution B correspond to the optimal pH.

2.1.4. Washing Patch

In still another example, there may be a washing patch. The washing patch is a patch that performs washing during a staining process and, somewhat different from the contact-type staining supplementary patch 100' described above, may not include a separate staining enhancing agent 160 or may use a small amount of water, alcohol, or the like as the staining enhancing agent 160.

The washing patch comes into contact with the specimen T to perform a role of removing foreign substances and the like remaining on the specimen T. For example, when a dye, a mordanting agent, a decolorizing agent, a fixing agent, or the like is applied to the specimen T during a staining process, some of whatever is applied remains on the specimen T and needs to be washed away. When the washing patch is brought into contact with the specimen T, the specimen T may be washed as a foreign substance is absorbed into a pore of the gel matrix of the washing patch. This is due to a property of the washing patch for absorbing a contacted foreign substance since the washing patch does not contain a solution and the like therein or contains only a small amount thereof.

Since the washing patch also performs a function of absorbing a liquid on the specimen T and simultaneously performs washing and drying the specimen T in the staining process, the washing patch may also be referred to as a drying patch.

Meanwhile, the washing and drying functions of the washing patch may also be performed by the buffering patch other than the washing patch. In a case of the buffering patch, since a relatively larger amount of solution is included inside the gel receptor 120 compared to the washing patch, performance of absorbing a foreign substance on the specimen T when brought into contact with the specimen T may be somewhat low. However, since the gel receptor 120 of the buffering patch also has some pores, the buffering patch may somewhat perform a function of absorbing residue on the specimen T. As a result, the buffering patch is able to perform some of washing and drying roles besides a buffering role in which an optimal pH is set with respect to the specimen T. Thus, buffering, washing, and drying are performed by only simply bringing the buffering patch into contact with the specimen T, and accordingly, the staining process can be simplified. Of course, performing separate washing and drying processes is possible when an excessive amount of residue is present.

Meanwhile, an absorbent may also be contained as the staining enhancing agent 160 in the gel receptor 120 of the washing patch to reinforce an absorption force of the washing patch. The porosity of the gel receptor 120 may be improved by not injecting a separate solution in the gel receptor 120 or injecting only a small amount of a solution therein as described above so that a foreign substance may be well-absorbed from the specimen T it contacts. However, when the absorbent is injected as the staining enhancing agent 160 in the gel receptor 120 to further improve the absorption force, an absorption rate may be improved by absorbing the foreign substance on the specimen T with which the absorbent has come into contact.

2.1.5. Composite Patch

Meanwhile, although each function of the contact-type staining supplementary patch 100' has been described above, the contact-type staining supplementary patch 100' may simultaneously have two or more functions in some cases.

For example, the buffering patch may simultaneously perform a role of buffering a reaction condition such as a pH concentration at the specimen T which is stained and a role of washing residue remaining on the specimen T. Although there is substantially almost no residue remaining at the specimen T when the specimen T is stained using the contact-type staining patch 100 according to an embodiment of the present disclosure, even an infinitesimal amount of residue that may be present at the specimen T may be clearly removed when the contact-type staining patch 100 is detached from the specimen T and then the buffering patch is brought into contact with the specimen T.

In addition, meanwhile, although it has been described above that the contact-type staining supplementary patch 100' is implemented with one patch for each role, one contact-type staining supplementary patch 100' may contain a composite staining enhancing agent 160 and perform two or more roles unlike the above description.

For example, the mordanting patch and the decolorizing patch may be implemented as one mordanting-and-decolorizing patch. The mordanting-and-decolorizing patch in which the mordanting agent and the decolorizing agent are simultaneously stored as staining enhancing agents 160 in the gel receptor 120 may simultaneously perform mordanting and decolorizing of the specimen T when brought into contact with the specimen T.

Furthermore, the contact-type staining patch 100 and the contact-type staining supplementary patch 100' may also be implemented by being combined with each other. For example, when the main staining agent, the mordanting agent, the decolorizing agent, and the contrast staining agent for the Gram staining technique may be accommodated in the gel receptor 120, the contact-type staining patch 100 and the contact-type staining supplementary patch 100' may be implemented using one patch (hereinafter referred to as a "composite patch").

The composite patch extremely simplifies the staining process, thus having an advantage of being convenient to use. However, when reactions occur between staining samples 140, between staining enhancing agents 160, and between the staining samples 140 and the staining enhancing agents 160 inside the gel receptor 120, staining may fail or an erroneously stained result may be obtained. Thus, the composite patch should be used in proper consideration of its advantages and disadvantages.

2.2. Method of Manufacturing a Contact-Type Staining Supplementary Patch

Hereinafter, a method of manufacturing the contact-type staining supplementary patch 100' according to an embodiment of the present disclosure described above will be described.

An example of the method of manufacturing the contact-type staining supplementary patch 100' may include forming the gel receptor 120 and absorbing the staining enhancing agent 160 into the gel receptor 120.

First, the gel receptor 120 is formed using a gel raw material that serves as a gel formation substance, a gelable substance, etc. such as agarose powder and the like. For example, the gel receptor 120 may be manufactured when agarose powder and water are mixed at a proper ratio, and the mixture is heated and cooled. Here, boiling the mixture, baking the mixture using a microwave, or the like may be used as the heating. In addition, here, the cooling may include natural cooling or forced cooling, and a stirring process may be included in the cooling as needed.

Next, the staining enhancing agent 160 can be absorbed into the manufactured gel receptor 120. To absorb the staining enhancing agent 160 into the gel receptor 120, a method in which the gel receptor 120 is dipped in a chamber, a container, or the like in which the staining enhancing agent 160 is accommodated for a predetermined amount of time and the gel receptor 120 is then taken out after the staining enhancing agent 160 is sufficiently absorbed thereinto may be used.

In another example, the method of manufacturing the contact-type staining supplementary patch 100' may include a method in which a gel raw material, an aqueous solution, and a staining sample are mixed to form a gel receptor. For example, the contact-type staining supplementary patch 100' may be manufactured by mixing agarose, an aqueous solution (or a buffering solution), and the staining enhancing agent 160 at a proper ratio, and heating and cooling the mixture. Here, the heating and cooling means may be similar to the examples described above.

In yet another example, the method of manufacturing the contact-type staining supplementary patch 100' may include a method in which a gel raw material and a solution are mixed and heated, and the staining enhancing agent 160 is then injected during a process of cooling the heated mixture. For example, after agarose and an aqueous solution are mixed at a proper ratio and heated, the staining enhancing agent 160 is injected during a process of cooling the heated mixture.

2.3. Experimental Example of the Contact-Type Staining Supplementary Patch

Hereinafter, an experimental example of the contact-type staining supplementary patch 100' according to an embodiment of the present disclosure described above will be described.

In this experimental example, the contact-type staining patch 100 and the contact-type staining supplementary patch 100' according to an embodiment of the present disclosure are applied in the conventional Giemsa staining technique for an examination for malaria.

Two contact-type staining patches 100 were manufactured to respectively have methylene blue and eosin which are Giemsa staining samples 140 as one sample.

Manufacturing a plurality of patches for each sample as above may have an advantage in which a storage period of the contact-type staining patch 100 is longer than in a case in which the patch is manufactured by mixing two staining samples 140 in one patch. To give a concrete example, when methylene blue and eosin are mixed and accommodated in one contact-type staining patch, methylene blue, which is basic, and eosin, which is acidic, may react with each other as time passes, and thus reactivity with respect to the specimen T may be degraded. On the other hand, when the contact-type staining patch 100 is separately manufactured for methylene blue and eosin, such a problem may be mitigated.

A specific manufacturing protocol is as follows.

1) After agarose, methylene blue, and the buffering solution B were mixed, the mixture was boiled or baked using a microwave and then cooled at room temperature to manufacture a methylene blue staining patch.

2) After agarose, eosin, and the buffering solution B were mixed, the mixture was boiled or baked using a microwave and then cooled at room temperature to manufacture an eosin staining patch.

In processes 1) and 2), agarose having a concentration of 1 to 5% was used, and a pH concentration of the buffering solution B was set as an optimal pH of the staining sample 140 in each case.

Then, the contact-type staining supplementary patch 100' was manufactured according to the following protocol.

3) After only agarose and the buffering solution B were mixed without the staining sample 140, the mixture was boiled or baked using a microwave and then cooled at room temperature to manufacture a buffering patch. Here, a PBS solution having a pH of 7.2 was used as the buffering solution B.

The methylene blue patch, the eosin patch, and the buffering patch manufactured as above were sequentially brought into contact with and detached from blood smeared on the slide S in that order. Here, the methylene blue patch was brought into contact with the blood for approximately thirty seconds and the eosin patch was brought into contact with the blood for approximately one minute. Then, the buffering patch was brought into contact with the blood for approximately three minutes.

Figure 13:
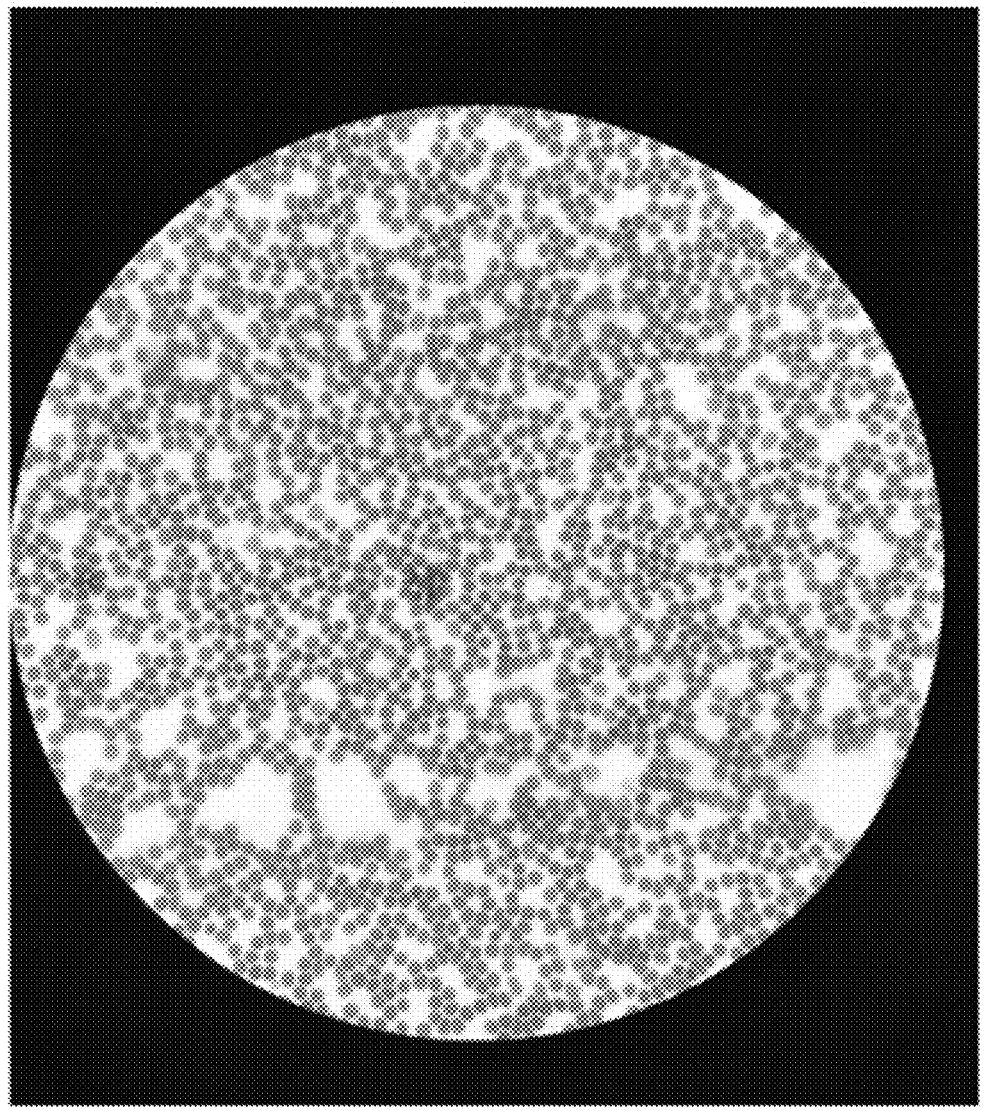
FIG. 13 is a view illustrating a staining result observed before a buffering patch is brought into contact with blood after a methylene blue patch and an eosin patch are brought into contact with the blood.
Figure 14:
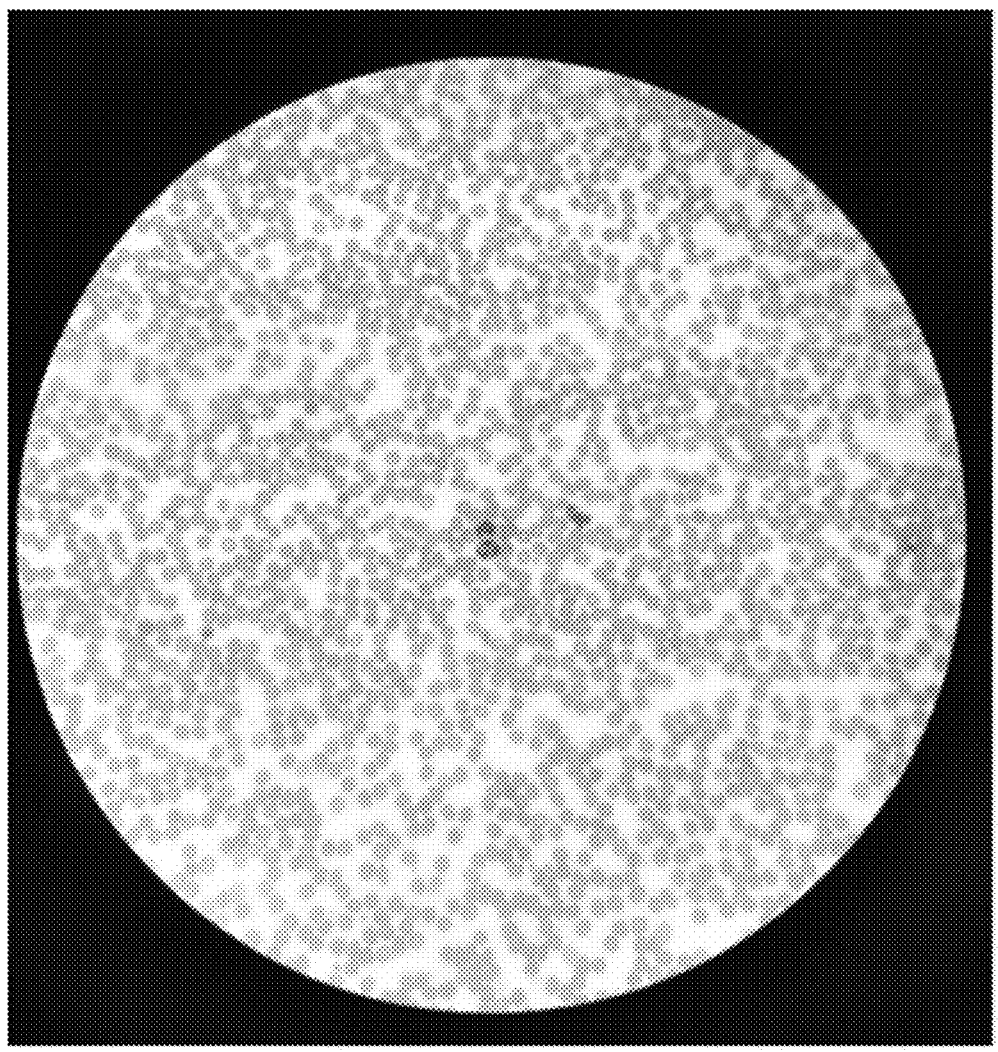
FIG. 14 is a view illustrating a staining result observed after the buffering patch is brought into contact with blood after the methylene blue patch and the eosin patch are brought into contact with the blood.

FIG. 13 is a view illustrating a staining result observed before a buffering patch is brought into contact with blood after a methylene blue patch and an eosin patch are brought into contact with the blood, and FIG. 14 is a view illustrating a staining result observed after the buffering patch is brought into contact with blood after the methylene blue patch and the eosin patch are brought into contact with the blood.

When FIGS. 13 and 14 are compared, it can be recognized that FIG. 13 is more similar to a result of normal staining according to a standard staining process of the Giemsa stain. Specifically, in FIG. 13, a blue color (methylene blue) is intensively stained compared to FIG. 14, and a red color stained by eosin is relatively not observed. This is because a reaction of eosin injected into blood later is hindered by methylene blue that has come into contact with blood before the eosin. When the buffering patch is brought into contact with blood in this state, normal staining is performed while decreasing an excessive reaction of methylene blue while increasing an insufficient reaction of eosin as a reaction condition (a pH concentration and the like) on the blood is adjusted to an optimal pH which is proper for the reaction.

In addition, when FIGS. 13 and 14 are closely examined, it can be recognized that stains and the like (an upper left side in FIG. 11) that were observed before the contact with the buffering patch were removed after the contact with the buffering patch.

In consideration of these points, when the staining samples 140 are used in combination, it can be recognized that the buffering patch simultaneously performs a function of properly creating a reaction condition so that each of the staining samples 140 reacts well and a washing function to remove a foreign substance.

In addition, since an excessive amount of the buffering solution B stored in the buffering patch is not moved toward blood, i.e., the specimen T, an additional drying procedure may be omitted or only a minimal drying procedure may be required.

3. Test Kit

Hereinafter, a test kit 1000 according to an embodiment of the present disclosure will be described.

The test kit 1000 according to an embodiment of the present disclosure may have the contact-type staining patch 100 stored therein to stain the specimen T when the specimen is injected thereinto.

3.1. Configuration of the Test Kit

The test kit 1000 may include two plates. Here, one of the two plates may be a plate 1200 (hereinafter, referred to as "patch plate") that stores the contact-type staining patch 100, and the other one of the two plates may be a plate 1400 (hereinafter, referred to as "specimen plate") that receives the specimen T.

In the test kit 1000, the two plates, i.e. the patch plate 1200 and the specimen plate 1400 may be coupled to be relatively movable. Here, moving is a concept that encompasses sliding or rotating.

In the test kit 1000, when the specimen T is injected onto the specimen plate 1400, the patch plate 1200 may move relative to the specimen plate 1400 so that the contact-type staining patch 100 stored in the patch plate 1200 is disposed on a point at which the specimen T is injected to bring the specimen T and the contact-type staining patch 100 into contact with each other to stain the specimen T.

Figure 15:
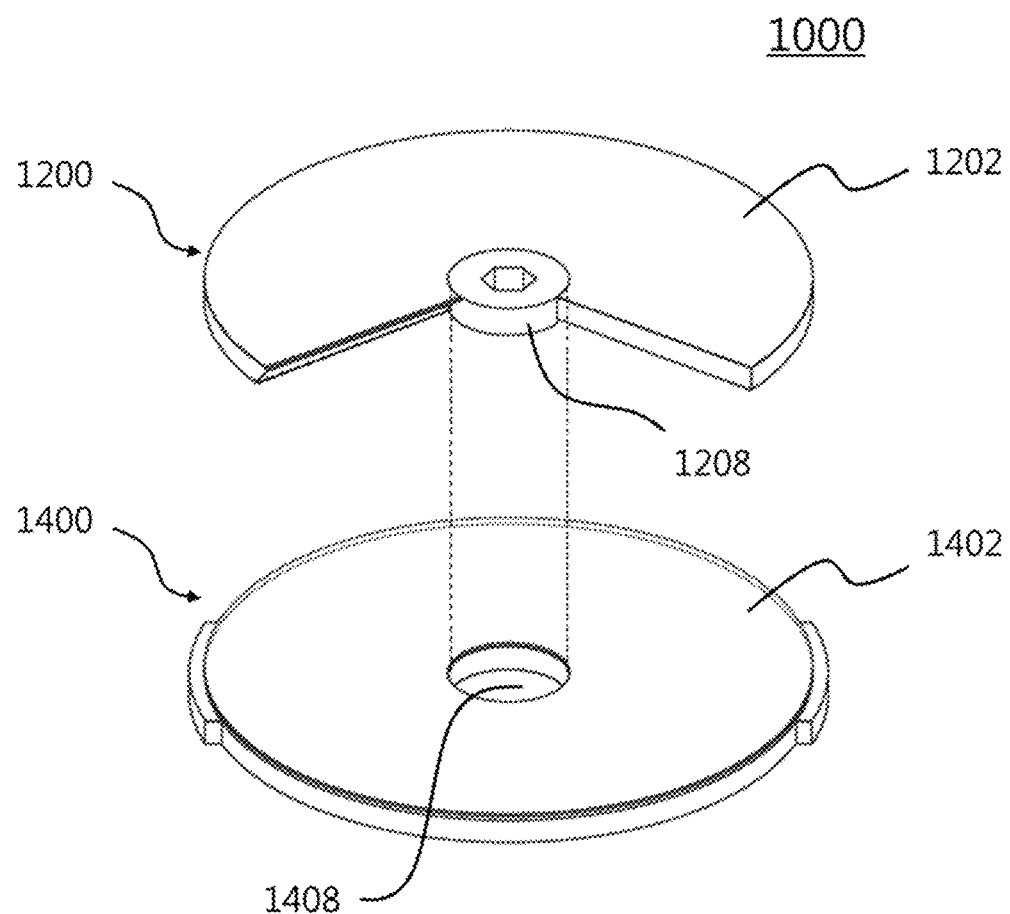
FIG. 15 is an exploded perspective view of an example of a test kit according to an embodiment of the present disclosure.
Figure 16:
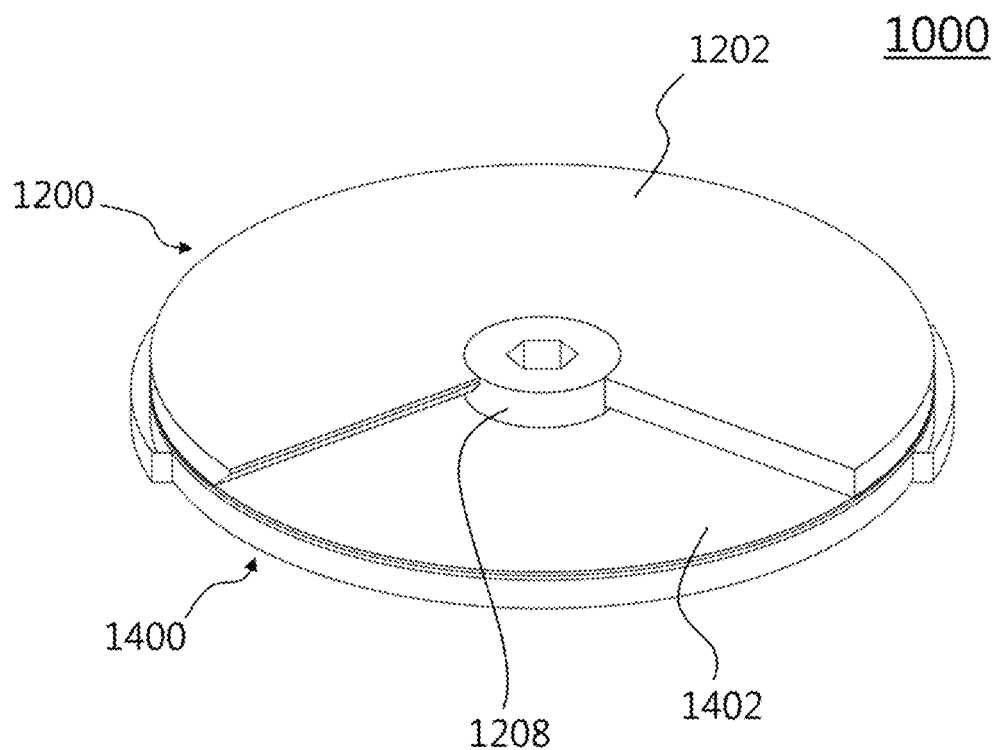
FIG. 16 is a coupled perspective view of the example of the test kit according to an embodiment of the present disclosure.

FIG. 15 is an exploded perspective view of an example of the test kit 1000 according to an embodiment of the present disclosure, and FIG. 16 is a coupled perspective view of the example of the test kit 1000 according to an embodiment of the present disclosure.

Referring to FIGS. 15 and 16, the specimen plate 1400 may have a disk-shaped body 1402 in the test kit 1000. In addition, the patch plate 1200 may have a body 1202 in the shape of a disk with an incised portion (e.g., a sector-shaped plate). The patch plate 1200 and the specimen plate 1400 may be provided to face each other and may be coupled to each other to be relatively rotatable at a central portion of the disk or the sector-shaped plate.

The bodies 1202 and 1402 of the patch plate 1200 and the specimen plate 1400 may each have an inner surface, an outer surface, and a side surface. Here, the inner surfaces are surfaces of the patch plate 1200 and the specimen plate 1400 that face each other, and the outer surfaces are surfaces opposite to the inner surfaces. That is, an inner surface 1204 of the patch plate 1200 is a surface close to the specimen plate 1400, an outer surface of the patch plate 1200 is a surface away from the specimen plate 1400, an inner surface 1404 of the specimen plate 1400 is a surface close to the patch plate 1200, and an outer surface of the specimen plate 1400 is a surface away from the patch plate 1200.

The patch plate 1200 and the specimen plate 1400 may be coupled to each other at central portions thereof. For example, as illustrated in FIGS. 15 and 16, a coupling protrusion 1208 that protrudes toward the inner surface may be formed on any one of the central portions of the patch plate 1200 and the specimen plate 1400, and a coupling hole 1408 or a coupling groove may be formed at the other central portion such that the patch plate 1200 and the specimen plate 1400 may be coupled to each other by inserting the coupling protrusion 1208 into the coupling hole 1408 or the coupling groove. Here, to stabilize coupling between the two plates, a nut may be connected to an end portion of the coupling protrusion that has passed through the coupling hole, a wing that extends from the end portion of the coupling protrusion in a diameter direction thereof may be formed, or the two plates may be coupled to each other using a separate pin.

Meanwhile, the patch plate 1200 and/or the specimen plate 1400 may be provided with a transparent or semitransparent material. When the patch plate 1200 and/or the specimen plate 1400 is transparent or semitransparent, there may be an advantage in which a tester can check a staining process using the test kit 1000 with his or her naked eye.

3.2. Structure of the Patch Plate

Figure 17:
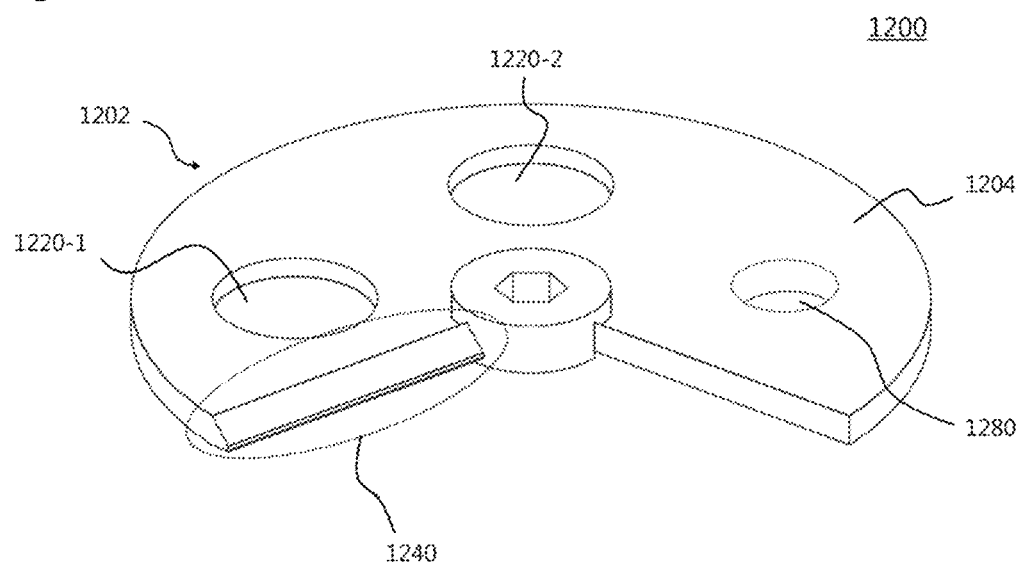
FIG. 17 is a perspective view of an example of a patch plate according to an embodiment of the present disclosure.

FIG. 17 is a perspective view of an example of the patch plate 1200 according to an embodiment of the present disclosure.

Referring to FIG. 17, the patch plate 1200 may have a body in the shape of a disk with an incised portion (e.g., a sector-shaped plate).

A storage unit 1220 that stores the contact-type staining patch 100 or the contact-type staining supplementary patch 100' may be formed at the body. Hereinafter, the contact-type staining patch 100 and the contact-type staining supplementary patch 100' will be collectively referred to as a "contact-type patch."

The storage unit 1220 may be formed on a sector-shaped area of the patch plate 1200 and, more particularly, may be formed at a position spaced apart from the center of the patch plate 1200 by a predetermined distance in a radial direction thereof.

One or a plurality of storage units 1220 may be formed at the patch plate 1200. For example, when attempting to stain blood according to the Giemsa staining technique, the number of storage units 1220 of the patch plate 1200 may be as follows. At the patch plate 1200, 1) only one storage unit 1220 for storing only a methylene blue-eosin patch (the contact-type staining patch 100 that simultaneously contains two staining samples 140, methylene blue and eosin) may be formed, 2) only two storage units 1220 for storing the methylene blue patch and an eosin patch, respectively, may be formed, or 3) three storage units 1220 for storing the methylene blue patch, the eosin patch, and a buffering patch, respectively, may be formed. For reference, FIG. 17 illustrates the patch plate 1200 at which two storage units 1220 are formed.

When there are the plurality of storage units 1220, an angle formed by each of the storage units 1220 with respect to the center of the patch plate 1200 when viewed in a direction of the inner surface of the patch plate 1200 may be uniform. For example, from the center of the patch plate 1200, an angle between a first storage unit 1220-1 and a second storage unit 1220-2 and an angle between the second storage unit 1220-2 and a third storage unit 1220-3 may be 45°. When angular intervals between the storage units 1220 are set to be equal to each other, there is an advantage of being easy to control a diagnostic device which will be described below since the contact-type patches can be sequentially brought into contact with the specimen T by being rotated the same as the angles.

The storage unit 1220 may store the contact-type staining patch 100 or the contact-type staining supplementary patch 100' so as to be exposed in a direction of the inner surface of patch plate 1200.

For example, as illustrated in FIG. 17, the storage unit 1220 may be formed in a form of a groove. The groove may be in a form in which the direction of the inner surface of the patch plate 1200 is open, i.e. a form recessed in the direction of the inner surface of the patch plate 1200. Accordingly, the contact-type patch to be stored in the storage unit 1220 may come into contact with the specimen T to be injected onto the specimen plate 1400.

Here, the groove may have a form corresponding to the contact-type patch to be stored therein.

Meanwhile, although the contact-type patch may be manufactured in various shapes, for convenience of description, a description will be given based on a contact-type patch manufactured in a cylindrical or polygonal cylindrical shape having main surfaces which are circular or polygonal upper surface, lower surface, and side surfaces that connect the upper surface and the lower surface to each other. Of course, the contact-type patch may also be manufactured in various other shapes including a hemispherical shape, a cylindrical or polygonal cylindrical shape in which sizes of an upper surface and a lower surface are different, and a cylindrical or polygonal cylindrical shape in which a side surface has a convex shape.

Figure 18:
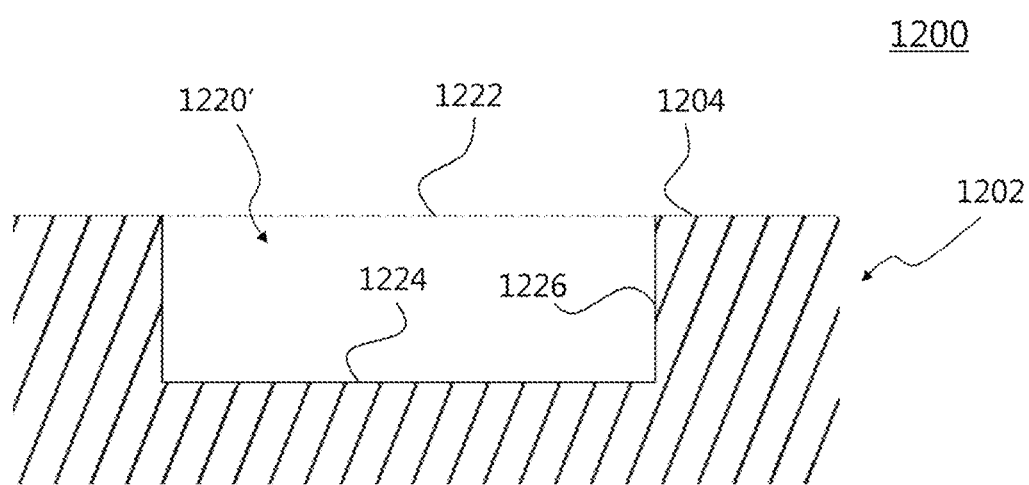
FIG. 18 is a cross-sectional view of an example of a storage unit in a groove form according to an embodiment of the present disclosure.

FIG. 18 is a cross-sectional view of an example of the storage unit 1220 in a groove form according to an embodiment of the present disclosure.

Referring to FIGS. 17 and 18, a groove 1220' may have an open surface 1222, a bottom surface 1224, and a side surface 1226.

When the groove 1220' is viewed in the direction of the inner surface 1204, the open surface 1222 and the bottom surface 1224 of the groove 1220' may have the same form as main surfaces of the contact-type patch. Here, when the groove 1220' is viewed in the direction of the inner surface 1204, at least one of the open surface 1222 and the bottom surface 1224 of the groove 1220' may have a size equal to or smaller than the main surfaces of the contact-type patch. When the size of the open surface 1222 or the bottom surface 1224 of the groove 1220' is smaller than that of the main surfaces of the contact-type patch, the storage unit 1220 may stably store the contact-type patch as the contact-type patch is stored in the groove in a somewhat compressed state.

A depth of the side surface 1226 of the groove 1220' may be the same or smaller than that of the contact-type patch. When the depth of the side surface 1226 of the groove 1220' is smaller than that of the contact-type patch, a portion of the contact-type patch stored in the groove protrudes from the inner surface of the patch plate 1200, and accordingly, contact between the contact-type patch and the specimen T on the specimen plate 1400 may be further facilitated.

A deviation preventing means that prevents the contact-type patch stored in the groove 1220' from deviating may be provided at the groove 1220'.

For example, the deviation preventing means may be implemented as a deviation preventing step that extends from the side surface 1226 touching the open surface 1222 of the groove 1220' toward a central portion of the open surface 1222. The contact-type patch stored in the storage unit 1220 is locked to the open surface 1222 of the groove by the deviation preventing step and thus is prevented from deviating to the outside.

In another example, the deviation preventing means may be implemented as a deviation preventing protrusion that extends from the side surface of 1226 of the groove 1220' toward the central portion of the groove 1220'. Due to being compressed and stored in the storage unit 1220 by the deviation preventing protrusion, the contact-type patch is stably fixed to the storage unit 1220, and thus does not deviate to the outside.

In yet another example, when the side surface 1226 of the groove 1220' is formed in a form of being gradually inclined from the bottom surface to the open surface toward the central portion of the groove 1220', the side surface 1226 may also perform a function of the deviation preventing means that prevents the contact-type patch stored in the groove 1220' from deviating to the outside instead of the deviation preventing means.

In addition, a contact guiding means 1228 that facilitates contact between the contact-type patch stored in the groove and the specimen T on the specimen plate 1400 may be provided at the bottom surface of the groove.

Figure 19:
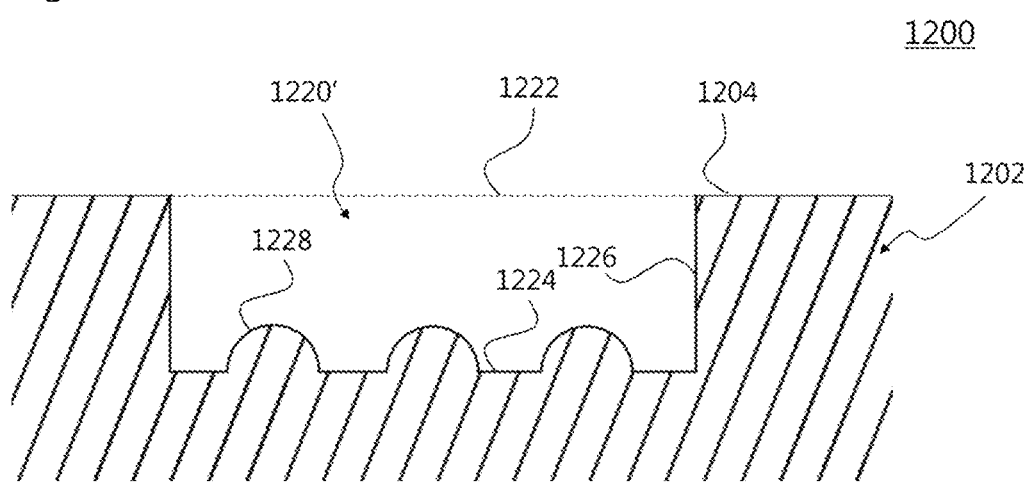
FIGS. 19 and 20 are cross-sectional views of the storage unit in a groove form having various contact guide means according to an embodiment of the present disclosure.
Figure 20:
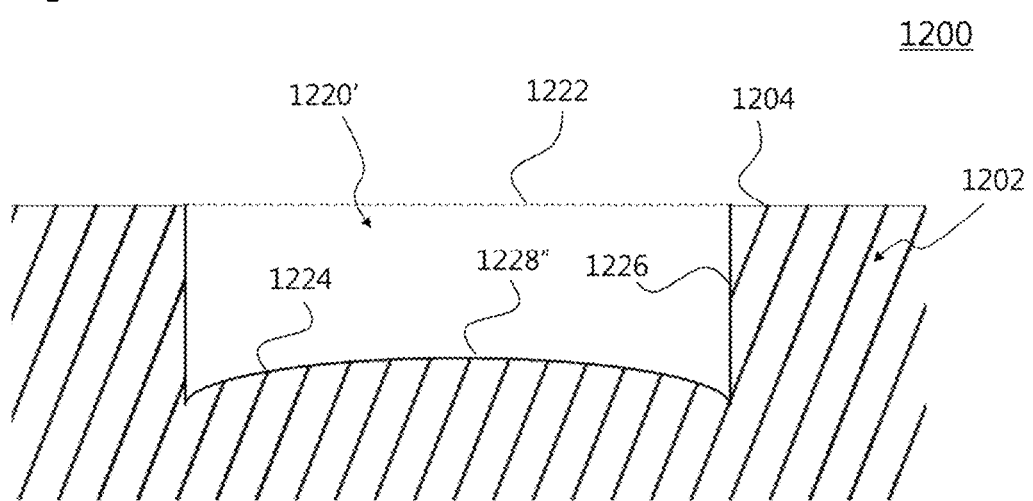

FIGS. 19 and 20 are cross-sectional views of the storage unit in a groove form having various contact guiding means according to an embodiment of the present disclosure.

For example, the contact guiding means 1228 may be implemented as a contact guiding protrusion 1228' that convexly protrudes from the bottom surface 1224 of the groove 1220' illustrated in FIG. 19. A portion of the contact-type patch stored in the storage unit 1220 protrudes from the inner surface of the patch plate 1200 by the contact guiding protrusion, and accordingly, contact with the specimen T on the specimen plate 1400 may be facilitated. The contact guiding protrusion 1228' does not always have to be in the form illustrated in FIG. 19, and, as illustrated in FIG. 20, the bottom surface 1224 of the groove 1220' itself may be formed as a convex surface 1228" and serve as the contact guiding means 1228.

Although the storage unit 1220 has been described above as being implemented in a groove form, unlike this, the storage unit 1220 may also be in a hole form.

The hole may have a first open surface formed at the inner surface of the patch plate 1200, a second open surface formed at the outer surface, and a side surface. Here, a deviation preventing means for preventing the contact-type patch stored in a direction of the second open surface from deviating may be provided at the second open surface. For example, the deviation preventing means may be implemented as a deviation preventing mesh.

Meanwhile, technical features (e.g., a size of an open surface, a depth of a groove, a deviation preventing step, a deviation preventing protrusion, etc.) mentioned in the description of the storage unit 1220 in a groove form may also be appropriately applied to the storage unit 1220 in a hole form. For example, a diameter of the hole may be equal to or less than that of the contact-type patch, a length of the hole may be equal to or less than the thickness of the contact-type patch, or a deviation preventing protrusion may be formed on the side surface of the hole.

3.3. Structure of the Specimen Plate

Figure 21:
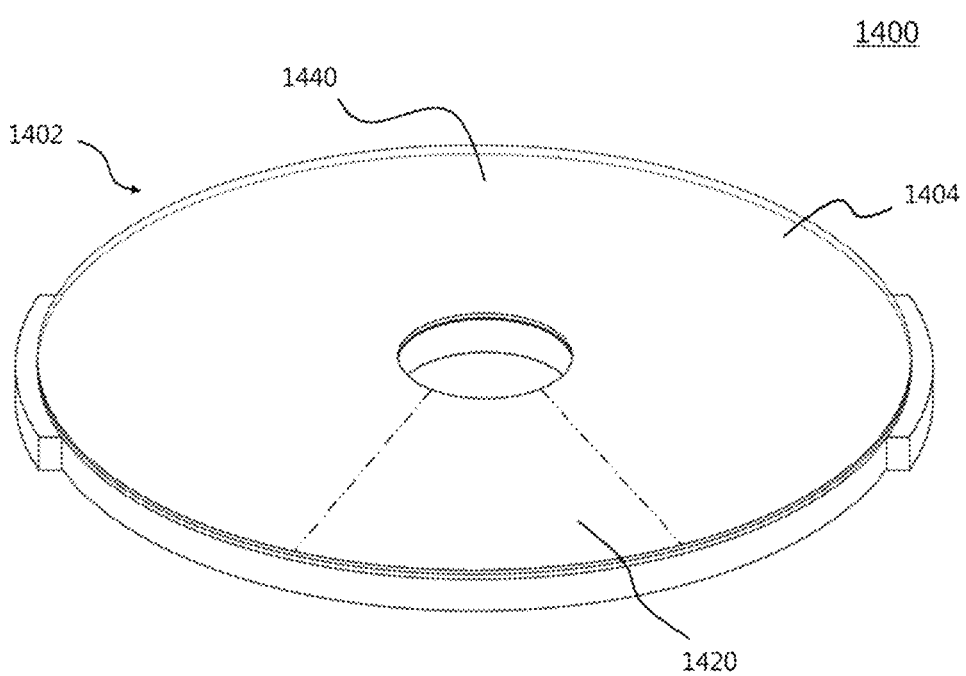
FIG. 21 is a perspective view of an example of a specimen plate according to an embodiment of the present disclosure.

FIG. 21 is a perspective view of an example of the specimen plate 1400 according to an embodiment of the present disclosure. Referring to FIG. 21, as described above, the specimen plate 1400 may have the disk-shaped body 1402 having the inner surface 1404, the outer surface, and the side surface. The inner surface 1404 is a surface facing the patch plate 1200 and may be provided in a circular shape in this embodiment.

A specimen area 1420 may be provided at a circular inner surface of the specimen plate 1400. Here, the specimen area 1420 is an area in which the specimen T injected into the test kit 1000 is placed. Although the specimen area 1420 may simply be an area into which the specimen T is injected, the specimen area 1420 should be viewed as an area that even includes an area in which the specimen T is smeared when the specimen T is smeared as in a blood smear examination. For example, when attempting to perform a blood smear examination, blood may be injected in a form of water drops into the specimen area 1420 and then smeared.

The specimen area 1420 may be provided in a specific area of an inner surface of a body of the specimen plate 1400. For example, the inner surface in a predetermined angular range with respect to the center of the disk may be the specimen area 1420.

Although it will be described below, the specimen T placed in the specimen area has to come into contact with the contact-type patch stored by the patch plate 1200 and has to be observed through an observation hole. For this, the specimen area 1420 needs to be aligned with each portion (the storage unit 1220, the observation hole, etc.) of the patch plate 1200 as the patch plate 1200 rotates relative to the specimen plate 1400.

In addition, in consideration of a case in which a blood smear examination is conducted using the test kit 1000, the specimen area 1420 needs to provide an area sufficient for injected blood to be smeared.

In consideration of these points, the specimen area 1420 may be provided in an area of approximately 45 to 90° of the inner surface. The area may be adjusted in consideration of the number of contact-type patches stored in the patch plate 1200, whether a blood smear examination is performed, etc.

Meanwhile, when a specimen is injected onto the specimen area 1420, the specimen T may be directly dropped onto the specimen area 1420. Here, an incised portion of the patch plate 1200 may be aligned at the specimen area 1420 so that the specimen area 1420 is exposed to the outside. For this, an angle range of the specimen area 1420 and an angle range of the incised portion of the patch plate 1200 may be adjusted to be equal to each other.

In addition, a surface of the specimen area 1420 may be specially treated. For example, the surface of the specimen area 1420 may be hydrophilic or hydrophobic. Specifically, the surface of the specimen area 1420 may be coated to be hydrophilic or hydrophobic, or a portion of the specimen area 1420 of the specimen plate 1400 may be prepared with a hydrophobic or hydrophilic material.

The specimen area 1420 is made to exhibit hydrophilia or hydrophobia in order to 1) allow the specimen area 1420 to hold the injected specimen T and/or 2) allow the specimen area 1420 to receive the staining sample 140, the buffering solution B, etc. from the contact-type patch. For example, when attempting to perform a blood smear examination using the Giemsa staining technique, the specimen area 1420 may be provided to be hydrophilic to hold injected blood and receive the Giemsa staining sample 140 from the contact-type staining patch 100.

A remaining area of the inner surface of the specimen plate 1400 except the specimen area 1420 may be a non-specimen area 1440. The non-specimen area 1440 may be an area in which the specimen T is not expected to be injected or smeared.

A surface of the non-specimen area 1440 may be treated to exhibit a property opposite from that of the surface of the specimen area 1420. For example, the non-specimen area 1440 may be hydrophobic when the specimen area 1420 is hydrophilic, and conversely, the non-specimen area 1440 may be hydrophilic when the specimen area 1420 is hydrophobic.

The non-specimen area 1440 is made to exhibit hydrophilia or hydrophobia in order to 1) inhibit the injected specimen T from being transferred to the non-specimen area 1440 and/or 2) prevent the staining sample 140, the buffering solution B, etc. from being transferred from the contact-type patch. Particularly, in a process in which the patch plate 1200 is rotated relative to the specimen plate 1400 to bring the contact-type patch into contact with the specimen T (even when a step exists between the specimen area 1420 and the non-specimen area 1440), the contact-type patch may sweep and pass across the non-specimen area 1440 of the specimen plate 1400. In this process, the staining sample 140 or the buffering solution B may be unnecessarily wasted by being transferred to the non-specimen area 1440 from the contact-type patch, or the contact-type patch may be contaminated due to a foreign substance on the non-specimen area 1440, and thus the non-specimen area 1440 is treated to be hydrophilic or hydrophobic to prevent the above situations. For example, when attempting to perform a blood smear examination using the Giemsa staining technique, the non-specimen area 1440 may be provided to be hydrophobic so that blood injected onto the specimen area 1420 is not transferred thereto and/or the Giemsa staining sample 140 is not transferred thereto from the contact-type staining patch 100.

Figure 22:
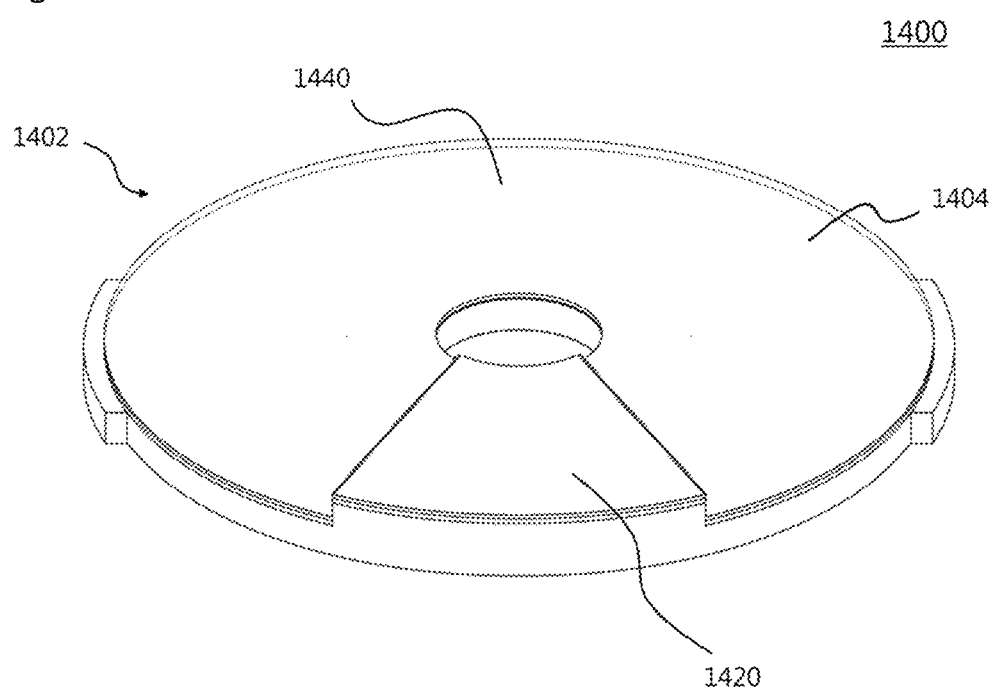
FIG. 22 is a perspective view of an example of a specimen plate with a step between a specimen area and a non-specimen area according to an embodiment of the present disclosure.

FIG. 22 is a perspective view of an example of the specimen plate 1400 with a step between the specimen area 1420 and the non-specimen area 1440 according to an embodiment of the present disclosure.

Referring to FIG. 22, the non-specimen area 1440 may have a lower height than that of the specimen area 1420. For example, a step may be formed at a boundary between the specimen area 1420 and the non-specimen area 1440. Thus, a distance between the inner surface of the patch plate 1200 and the inner surface of the specimen plate 1400 corresponding to the non-specimen area 1440 may be larger than a distance between the inner surface of the patch plate 1200 and the inner surface of the specimen plate 1400 corresponding to the specimen area 1420.

During a process in which the specimen T and the contact-type patch are brought into contact with each other, the patch plate 1200 is rotated relative to the specimen plate 1400 so that the contact-type patch can be aligned with the specimen area 1420. When there is a step between the specimen area 1420 and the non-specimen area 1440, the contact-type patch may be prevented from sweeping and passing across the non-specimen area 1440 of the specimen plate 1400 during the rotation of the patch plate 1200 while the contact between the contact-type patch and the specimen T on the specimen area 1420 is easily maintained. Accordingly, the staining sample 140 or the buffering solution B of the contact-type patch may be prevented from being wasted due to being transferred to the non-specimen area 1440 and contamination of the contact-type patch due to contact with the non-specimen area 1440 may be inhibited.

3.4. Smearing Unit

Meanwhile, the test kit 1000 may further include a smearing unit 1240 that smears the specimen T injected onto the specimen area 1420. Hereinafter, the smearing unit 1240 that smears the specimen will be described.

In a conventional staining technique, smearing of the specimen T is performed by a tester's manual work.

Figure 23:
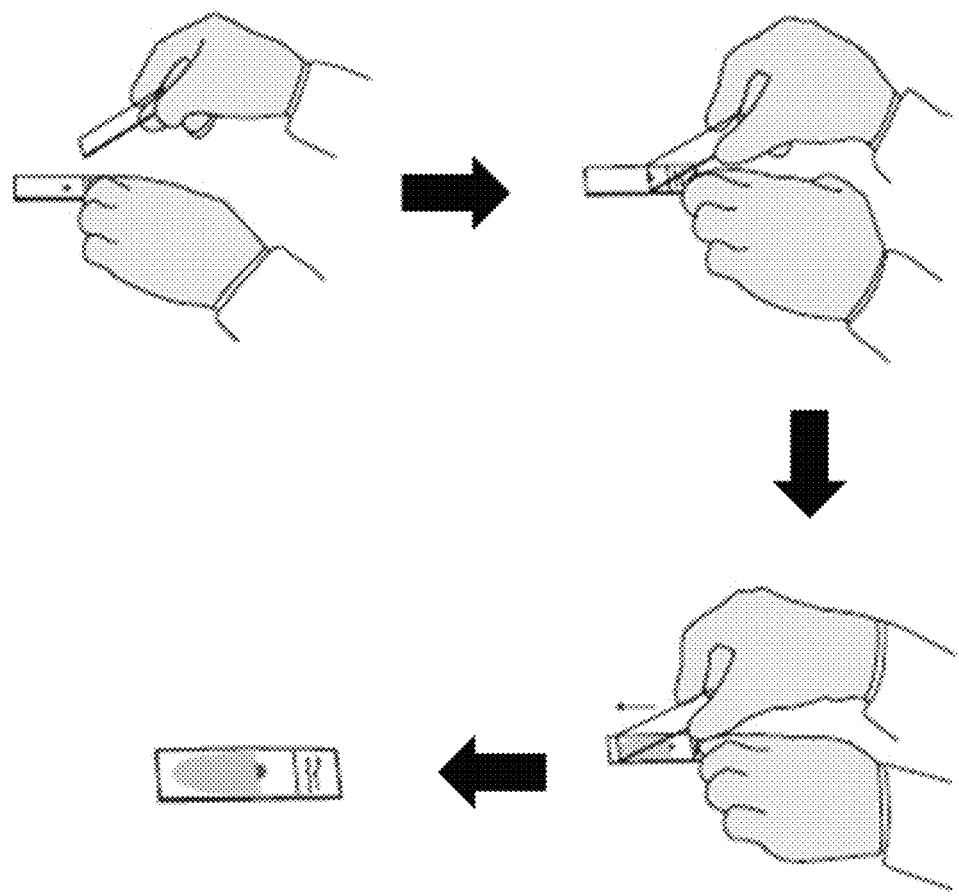
FIG. 23 is a view illustrating a blood smearing means according to the conventional blood smear examination process.

FIG. 23 is a view illustrating a blood smearing means according to the conventional blood smear examination process.

Referring to FIG. 23, in the conventional blood smear examination process, the specimen T is first placed on the slide S and then another slide is brought into contact with the slide S on which the specimen T is placed so that an acute angle is formed therebetween. Then, when a tester slides the slide S on which the specimen T is placed while an end of the other slide remains in contact with the specimen T, the specimen T may be spread on the slide S and smeared. The angle between the slides and a sliding speed need to be properly adjusted to smear the specimen T in a desired form (e.g., a monolayer). Conventionally, there is a problem of low stability due to the factors above totally depending on the tester.

Figure 24:
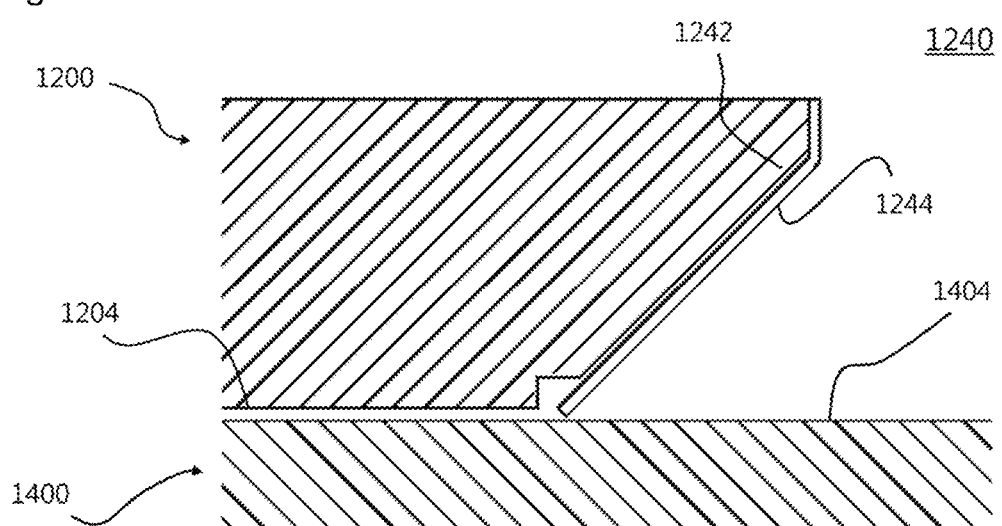
FIG. 24 is a cross-sectional view of a smearing unit of the test kit according to an embodiment of the present disclosure.

FIG. 24 is a cross-sectional view of the smearing unit 1240 of the test kit 1000 according to an embodiment of the present disclosure.

Referring to FIG. 24 in addition to FIGS. 15 to 17, the smearing unit 1240 may be provided at any one side the incised portion of the patch plate 1200. The smearing unit 1240 may perform a function of smearing the specimen T placed on the specimen area 1420.

The smearing unit 1240 may include an inclined surface 1242 that forms an acute angle with the inner surface of the specimen plate 1400 that faces the inclined surface 1242 when viewed from a side surface and a smearing film 1244 attached to the inclined surface 1242.

Hereinafter, a specimen smearing process using the smearing unit 1240 will be briefly described. However, for convenience of description, the description will be given based on a blood smear.

FIG. 25 is a view illustrating a blood smearing process using the smearing unit 1240 of the test kit 1000 according to the embodiment of the present disclosure.

First, as in (a) of FIG. 25, blood is injected onto the specimen area 1420 of the specimen plate 1400. Here, the incised portion of the patch plate 1200 and the specimen area 1420 of the specimen plate 1400 are aligned with each other so that the specimen area 1420 is exposed to the outside.

When the blood is injected, as in (b) of FIG. 25, the patch plate 1200 is rotated with respect to the specimen plate 1400 (the direction of this rotation is defined as a "reverse direction") so that the smearing unit 1240 is moved toward a spot into which blood is injected. As a result, the smearing film 1244 and a blood drop placed on the specimen area 1420 come into contact with each other.

When the smearing film 1244 and the blood come into contact with each other, the blood spreads between the smearing film 1244 and the surface of the specimen area 1420 along the smearing film 1244 in a direction in which the patch plate 1200 is incised due to a capillary phenomenon. When the patch plate 1200 is a sector-shaped plate in which a disk is cut in the diameter direction, the blood spreads in the diameter direction.

When the patch plate 1200 is rotated in a forward direction (opposite of the reverse direction) with respect to the specimen plate 1400 while the blood is spread, the blood may move along the smearing film 1244 and be smeared as illustrated in (c) of FIG. 25.

Here, the inclined surface of the smearing unit 1240 may preferably have an inclined angle of approximately 10 to 60° with respect to the inner surface of the specimen plate 1400.

The size of the inclined angle may be properly adjusted according to a property of the specimen T.

When the inclined angle is too large (e.g., a right angle), it may be difficult for the capillary phenomenon to occur in a step in which the smearing film 1244 and the specimen T come into contact with each other (the step illustrated in (b) of FIG. 25), and the specimen T may not sufficiently spread in the direction in which the patch plate 1200 is incised. In addition, even when attempting to smear the specimen T by a forward rotation, smearing may not be properly performed due to the blood not following the smearing film 1244.

On the other hand, when the inclined angle is too small, the capillary phenomenon may not properly occur due to the smearing film 1244 and the specimen T coming into contact with each other at a portion other than a lower end portion of the smearing film 1244, and smearing may not be performed due to the blood not properly following the smearing film 1244.

A material that can be easily followed by the specimen T may be used for the smearing film 1244. For example, when the specimen T is blood, a hydrophilic material should be used for the smearing film 1244 so that the blood is smeared by following the smearing film 1244 during the forward rotation of the patch plate 1200. When a hydrophobic smearing film 1244 is used for the specimen T which is blood, smearing may not be performed.

When viewed from the top, the smearing film 1244 may be attached and installed along the direction in which the patch plate 1200 is incised. When viewed from the top, the smearing film 1244 should have a length of an extent to which the specimen T can sufficiently spread according to the capillary phenomenon in the direction in which the patch plate 1200 is incised. For example, the smearing film 1244 may have a length of about 30 to 100% of an incised surface in the diameter direction.

When viewed from the side surface, the smearing film 1244 may be attached and installed at the inclined surface along the inclined angle thereof. Here, the smearing film 1244 is installed so it can touch the inner surface of the specimen plate 1400. Accordingly, the smearing film 1244 may cause the capillary phenomenon at the specimen T.

Although it would be theoretically preferable that the lower end of the smearing film 1244 be manufactured to accurately come into contact with the inner surface of the specimen plate 1400, this is actually impossible in consideration of manufacture tolerance and the like or high cost would be required.

Consequently, for the smearing film 1244 to come into contact with the specimen area 1420, the smearing film 1244 may be installed in a way in which a lower portion thereof protrudes from the inner surface of the patch plate 1200 in the direction of the inner surface of the specimen plate 1400. According to this, since the smearing film 1244 has some degree of flexibility, the smearing film 1244 may come into contact with the specimen area 1420 because the lower portion of the smearing film 1244 is curled in a bent form. In addition to this, a groove may be formed at a lower portion of the inclined surface as a space in which a curled portion of the smearing film 1244 is accommodated.

Meanwhile, although it has been described above that the tester directly drops the specimen T on the specimen area 1420 when the specimen T is being injected, unlike this, a loading unit 1250 through which the specimen T is injected may also be provided.

Figure 26:
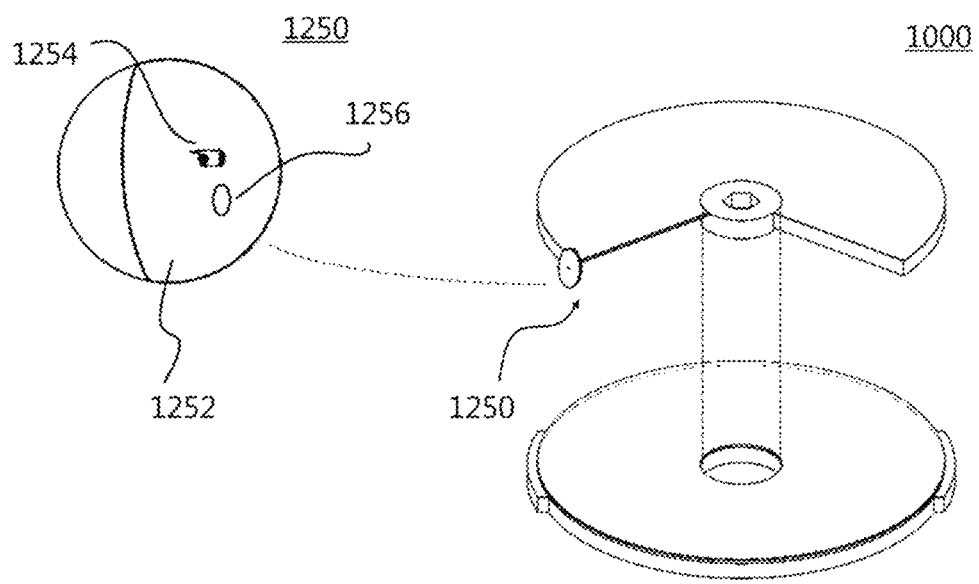
FIG. 26 is a view illustrating a loading unit of the test kit according to an embodiment of the present disclosure.
Figure 27:
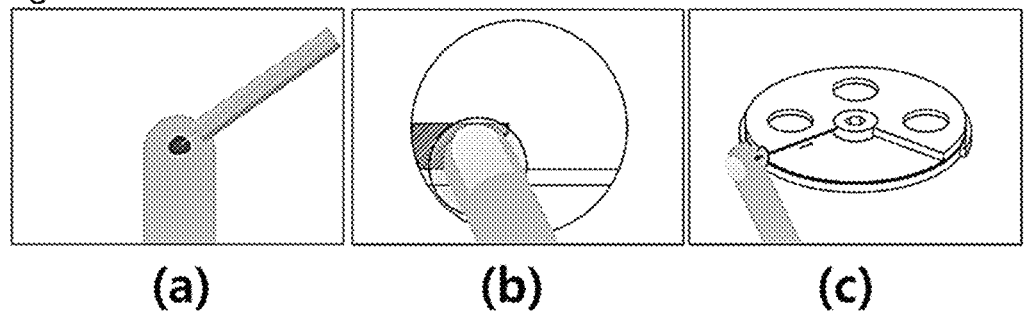
FIG. 27 is a view related to loading of a specimen using the loading unit according to an embodiment of the present disclosure.

FIG. 26 is a view illustrating the loading unit 1250 of the test kit 1000 according to an embodiment of the present disclosure, and FIG. 27 is a view related to loading of the specimen T using the loading unit 1250 according to an embodiment of the present disclosure.

Referring to FIG. 26, the loading unit 1250 may include a pressing plate 1252, a collecting pin 1254, and a loading hole 1256.

The pressing plate 1252 is a portion pressed by a testee's body part from which the specimen T will be collected. For example, when attempting to collect blood from a person's fingertip, the pressing plate 1252 may be provided in the shape of a plate having a proper size to be pressed by the person's fingertip. The pressing plate 1252 may be installed at a position which enables the collected specimen T to be transferred to the specimen area 1420 of the specimen plate 1400. For example, the pressing plate 1252 may be disposed at an outer edge portion of the incised surface of the patch plate 1200 or an outer edge portion of the specimen area 1420.

The collecting pin 1254 is a pin installed to protrude from the pressing plate 1252. During a process in which the testee's body part presses the pressing plate 1252, the collecting pin 1254 pierces skin at the body part to allow the specimen T to be collected from the testee. The collecting pin 1254 may preferably be disposed at a central portion of the pressing plate 1252 and be installed toward an outer direction of the test kit 1000.

The loading hole 1256 is formed in the form of a hole that passes through the pressing plate 1252 and may be formed by passing from an outer surface (a surface coming into contact with the testee's body part) to the opposite surface thereof of the pressing plate 1252. Accordingly, the loading hole 1256 may load the specimen T from an outside of the pressing plate 1252 to an inside of the test kit 1000, more specifically, toward the specimen area 1420 or the smearing unit 1240 of the specimen plate 1400. The loading hole 1256 may be formed near the collecting pin 1254 and receive the specimen T collected from the testee's skin by the collecting pin 1254, and may transfer and inject the specimen T toward the specimen area 1420 or the smearing unit 1240 according to the capillary phenomenon.

The loading of the specimen T may be performed as follows.

First, when a testee presses the pressing plate 1252 with a finger as illustrated in (b) of FIG. 27, blood comes out of skin of the finger by the collecting pin 1254. As illustrated in (c) of FIG. 27, the blood is transferred through the loading hole 1256 to the outside of the specimen area 1420 that comes into contact with the smearing film 1244. The transferred blood is transferred to the inside of the specimen area 1420 by the capillary phenomenon between the smearing film 1244 and the specimen area 1420. Then, the patch plate 1200 may be rotated in the forward direction with respect to the specimen plate 1400 to smear the blood.

When the loading unit 1250 is used in this way, the specimen T may be injected into the test kit 1000 by only simply pressing the loading unit with a testee's body part instead of a tester directly injecting the specimen T into the specimen area 1420.

Meanwhile, the collecting pin 1254 may be omitted from the pressing plate 1252 in the process of loading the specimen T described above. In this case, as in (a) of FIG. 27, before the pressing plate 1252 is pressed using the testee's body part, a separate pin may be used to allow the specimen T to be collected from the corresponding body part.

3.5. Rotating and Lifting Operations of the Test Kit

It has been mentioned above that the process of staining the specimen T can be carried out by bringing the contact-type patch into contact with the specimen T injected into the specimen plate 1400 while the patch plate 1200 rotates relative to the specimen plate 1400.

Specifically, a process of bringing the contact-type patch and the specimen T into contact with each other may be carried out by 1) rotating the patch plate 1200 relative to the specimen plate 1400 to place the contact-type patch on the specimen T or the specimen T which is smeared; and 2) lowering patch plate 1200 relative to the specimen plate 1400 so that the contact-type patch stored in the patch plate 1200 comes into contact with the specimen T.

The patch plate 1200 and the specimen plate 1400 are basically coupled in a way in which the inner surfaces thereof are spaced apart from each other in a predetermined interval. This is to prevent the contact-type patch stored in the patch plate 1200 from being swept by the specimen plate 1400 during a rotation process. Consequently, after the contact-type patch is placed on the specimen T, the patch plate 1200 and the specimen plate 1400 should be adhered to each other to bring the contact-type patch into contact with the specimen T.

For this, lifting guides 1260 and 1460 may be formed at the patch plate 1200 and/or the specimen plate 1400. The lifting guides 1260 and 1460 may lift the patch plate 1200 and the specimen plate 1400 according to relative rotations of the patch plate 1200 and the specimen plate 1400.

Figure 28:
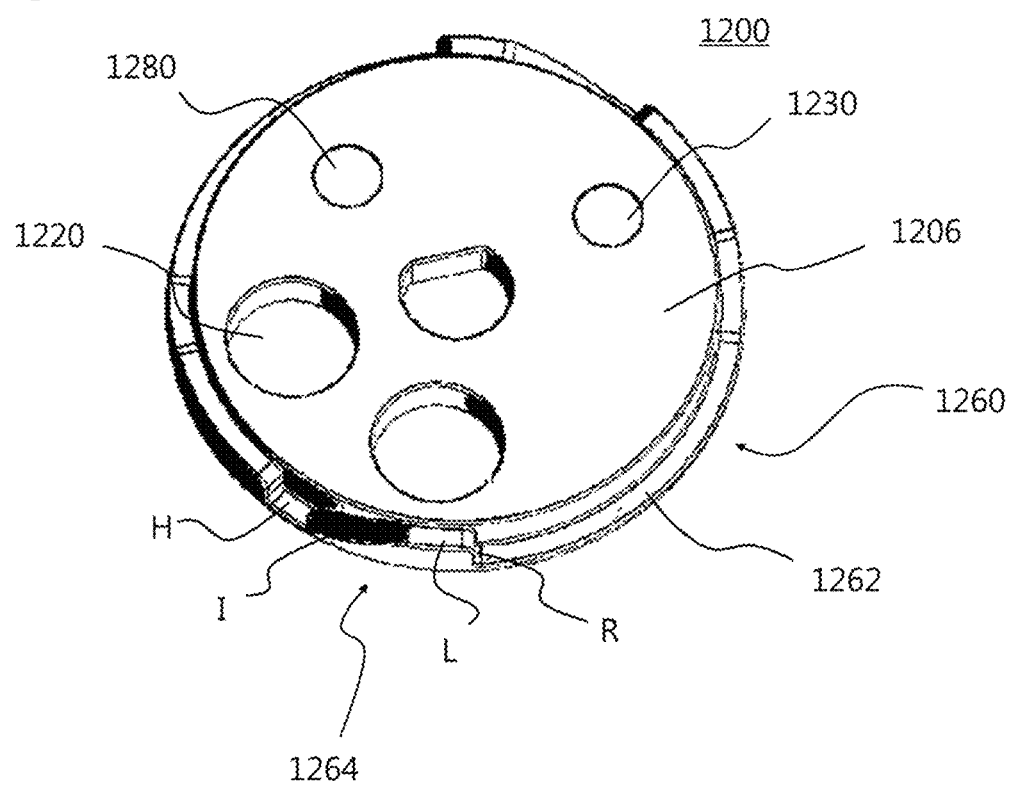
FIG. 28 is a perspective view of a patch plate having a lifting guide according to an embodiment of the present disclosure.
Figure 29:
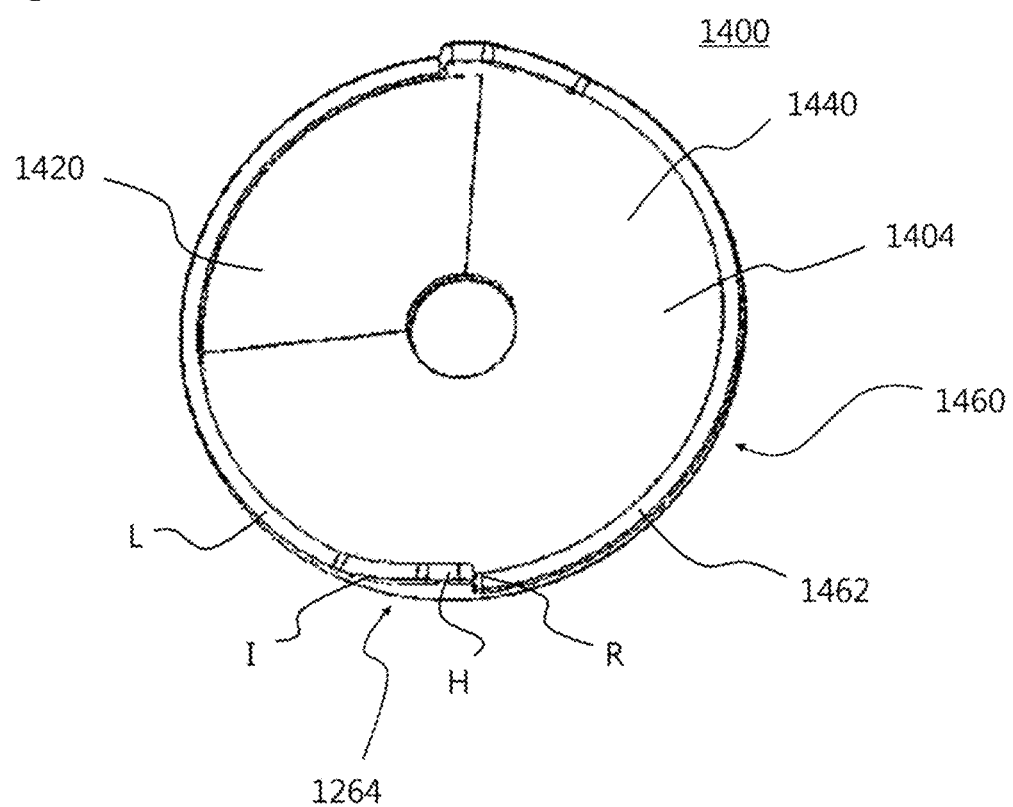
FIG. 29 is a perspective view of the specimen plate having the lifting guide according to an embodiment of the present disclosure.

FIG. 28 is a perspective view of the patch plate 1200 having the lifting guide 1260 according to an embodiment of the present disclosure, and FIG. 29 is a perspective view of the specimen plate 1400 having the lifting guides 1460 according to an embodiment of the present disclosure.

Referring to FIGS. 28 and 29, the lifting guides 1260 and 1460 may be formed at outsides of the bodies of the patch plate 1200 and the specimen plate 1400. The lifting guides 1260 and 1460 formed at the two plates may respectively include base plates 1262 and 1462 formed to surround circumferences of the bodies and lifting patterns 1264 and 1464 formed in predetermined patterns on the base plates 1262 and 1462.

The base plates 1262 and 1462 are formed to surround outer circumferential surfaces of the bodies of the patch plate 1200 and the specimen plate 1400 with smaller thicknesses than the patch plate 1200 and the specimen plate 1400. In other words, the base plates 1262 and 1462 are bent with steps from circumferences of the inner surfaces of the patch plate 1200 and the specimen plate 1400 toward the outer surfaces thereof to form edges of the patch plate 1200 and the specimen plate 1400.

Meanwhile, in FIG. 28, a disk-shaped body may be used instead of the incised sector-shaped body for the patch plate 1200. In this case, the specimen T may be transferred to the specimen plate 1400 through a specimen injection hole 1230 instead of being dropped through the incised portion. In addition, although it has been described that the coupling protrusion is formed at the patch plate 1200, a coupling hole instead of the coupling protrusion may be formed in FIG. 28. The coupling hole communicates with a coupling hole at the specimen plate 1400, and the two plates may be coupled to each other by a coupling pin fitted into a communication passage. Here, it should be noted that both of the sector-shaped form and the disk-shaped body according to FIG. 28 are modified examples not departing from the spirit of the present disclosure.

The lifting patterns 1264 and 1464 may be formed protruding or being recessed from the base plates. The lifting patterns 1264 and 1464 may perform roles of adjusting an interval between the inner surfaces of the two plates according to relative angles between the two plates while the two plates are coupled to each other.

The lifting patterns 1264 and 1464 may each include a high point part H, a low point part L, a sloped part I, and a stepped part R. Here, the high point part H is the highest part of the lifting patterns 1264 and 1464, and the low point part L is the lowest part of the lifting patterns. For example, the high point part H may be a part that protrudes the most from the base plates, and the low point part L may be a part that does not protrude from the base plates. The sloped part I may be a part with a slope that gradually increases from the low point part toward the high point part. The stepped part R may be a part perpendicularly bent from the high point part H toward the low point part L.

When the patch plate 1200 rotates with respect to the specimen plate 1400, the patch plate 1200 may be lifted with respect to the specimen plate 1400 as the lifting pattern of the patch plate 1200 moves along an upper portion of the lifting pattern of the specimen plate 1400. Here, lifting refers to an interval between the two plates being narrowed or widened. The patch plate 1200 moving away from the specimen plate 1400 is defined as "ascending," and the patch plate 1200 approaching the patch plate 1400 is defined as "descending."

A state in which the high point part of the specimen plate 1400 is aligned with the low point part of the other plate is a state in which the patch plate 1200 is maximally descended with respect to the specimen plate 1400, i.e. a state in which the interval between the two plates is minimal.

A state in which the high point part of the specimen plate 1400 is aligned with the high point part of the patch plate 1200 is a state in which the patch plate 1200 is maximally ascended with respect to the specimen plate 1400, i.e. a state in which the interval between the two plates is maximal.

In addition, while the high point part of the specimen plate 1400 moves from the low point part of the patch plate 1200 toward the high point part of the patch plate 1200 along the sloped part of the patch plate 1200, the patch plate 1200 gradually ascends with respect to the specimen plate 1400. Conversely, while the high point part of the specimen plate 1400 moves from the high point part of the patch plate 1200 toward the low point part of the patch plate 1200 along the sloped part of the patch plate 1200, the patch plate 1200 gradually descends with respect to the specimen plate 1400.

In addition, when the high point part of the specimen plate 1400 passes the stepped part of the patch plate 1200 in a direction from the high point part of the patch plate 1200 toward the low point part of the patch plate 1200, the patch plate 1200 perpendicularly descends with respect to the specimen plate 1400.

Conversely, when the stepped part is formed at the patch plate 1200 and the high point part of the specimen plate 1400 attempts to move in a direction from the low point part of the patch plate 1200 toward the high point part of the patch plate 1200, a rotation of the patch plate 1200 relative to the specimen plate 1400 may be inhibited by the stepped part.

The test kit 1000 may be designed in a way in which the contact-type patch stored in the patch plate 1200 comes into contact with at least a portion of the inner surface of the specimen plate 1400 when the patch plate 1200 is maximally descended with respect to the specimen plate 1400, and hereinafter, this is defined as a "contact state." For example, in the contact state, the contact-type patch stored in the storage unit 1220 may come into contact with the specimen T placed in the specimen area 1420.

In addition, the test kit 1000 may be designed in a way in which the contact-type patch stored in the patch plate 1200 does not come into contact with the inner surface of the specimen plate 1400 at states other than that in which the patch plate 1200 is maximally descended with respect to the specimen plate 1400, and hereinafter, this is defined as a "separated state." For example, in the separated state, the contact-type patch stored in the storage unit 1220 may not come into contact with the non-specimen area 1440.

In consideration of the principles above, the lifting patterns may be designed as follows.

The lifting patterns may be designed so that the contact state is reached at an angle at which the storage unit 1220 of the patch plate 1200 is aligned with the specimen area 1420 of the specimen plate 1400. Accordingly, the contact-type patch stored in the storage unit 1220 may come into contact with the specimen T.

In addition, the lifting patterns may be designed so that the contact state is not reached at an angle at which the storage unit 1220 of the patch plate 1200 is at an upper portion of the non-specimen area 1440 of the specimen plate 1400. Accordingly, the contact-type patch stored in the storage unit 1220 may not come into contact with the non-specimen area 1440.

Referring again to FIG. 29, the lifting pattern of the specimen plate 1400 may be formed as follows.

The high point part is disposed at one or more portion of the edge of the specimen area 1420. Here, the portion may be the edge of the specimen area 1420 at which the specimen is placed, or may be the edge at a central point of an area in which the specimen T is smeared when the specimen T is smeared. The lifting pattern may be formed so that the low point part is disposed at the edge of the non-specimen area 1440. The sloped part or the stepped part may be disposed between the high point part and the low point part.

Referring again to FIG. 28, the lifting pattern of the patch plate 1200 may be formed as follows. FIG. 28 illustrates the patch plate 1200 in an outer surface direction.

The low point part is disposed at a portion of an edge of the storage unit 1220. Here, the portion may be an edge in the diameter direction from the center of the patch plate 1200 toward the center of the storage unit 1220. The high point part is disposed at remaining parts of the edge of the patch plate 1200. The sloped part or the stepped part may be disposed between the high point part and the low point part.

According to the lifting patterns, the test kit 1000 may operate as follows.

First, the incised portion of the patch plate 1200 may be disposed at an upper portion of the specimen area 1420 of the specimen plate 1400 such that the specimen area 1420 is exposed to the outside. A tester may directly drop the specimen T onto the exposed specimen area 1420. When the specimen T is dropped, the patch plate 1200 is rotated in the reverse direction with respect to the specimen plate 1400 to bring the smearing unit 1240 into contact with the specimen T so that the specimen T is spread along the smearing unit 1240. When the specimen T is spread, the patch plate 1200 may be rotated in the forward direction to smear the specimen T. During this process, the high point part of the specimen plate 1400 is in contact with the high point part of the patch plate 1200, and accordingly, the storage unit 1220 is not in contact with the inner surface (the non-specimen area 1440) of the specimen plate 1400.

When the patch plate 1200 is further rotated in the forward direction after the smearing is completed, the high point part of the specimen plate 1400 comes into contact with the low point part of the patch plate 1200 disposed at the edge of the storage unit 1220, and accordingly, the two plates reach the contact state and the contact-type patch stored in the storage unit 1220 comes into contact with the specimen T at the specimen area 1420.

Here, the stepped part may be provided between the high point part at the edge of the smearing unit 1240 and the low point part of the storage unit 1220. Accordingly, while passing through the stepped part, the patch plate 1200 perpendicularly descends with respect to the specimen plate 1400, and thus the contact-type patch may come into contact with the specimen T by being stamped thereon. In addition, after the stamping of the contact-type patch, a reverse rotation of the patch plate 1200 may be inhibited by the stepped part.

When the patch plate 1200 is further rotated in the forward direction after the stamping, the high point part of the specimen plate 1400 passes the sloped part of the patch plate 1200. Accordingly, the contact-type patch is separated from the specimen T as the patch plate 1200 ascends from the specimen plate 1400.

The high point part of the specimen plate 1400 comes into contact with the high point part of the patch plate 1200 again after passing the sloped part of the patch plate 1200, and the separation is completed. Accordingly, when the contact-type patch stored in the patch plate 1200 passes an upper portion of the non-specimen area 1440, the contact-type patch may not come into contact with the inner surface of the specimen plate 1400.

When there are one or more storage units 1220, the patch plate 1200 may be further rotated in the forward direction. Here, the high point part of the specimen plate 1400 comes into contact with the low point part of the patch plate 1200 according to the next storage unit 1220, and thus the next contact-type patch comes into contact with the specimen T. This process may be similarly followed by the stamping process and the process in which the contact-type patch is separated from the specimen T by the sloped part described above.

When the patch plate 1200 is further rotated in the forward direction after the specimen T is brought into contact with all contact-type patches provided in the test kit 1000, the high point part of the specimen plate 1400 comes into contact with the low point part formed at an edge of an observation unit of the patch plate 1200.

Here, the observation unit may be formed with an observation hole formed at one spot of the patch plate 1200, and the tester may observe and examine the specimen T which is completely stained, and the like, using a microscope, or the like.

According to the present disclosure, when staining a specimen, the specimen is stained by only bringing a contact-type staining patch into contact with the specimen instead of spraying a staining solution such that a staining process can become convenient.

In addition, according to the present disclosure, a pore in a gel receptor of a contact-type staining patch stores a staining sample and inhibits external contamination or leakage such that staining can be performed using a contact-type staining patch manufactured in advance prior to staining at a desired time.

In addition, according to the present disclosure, a staining sample is well-preserved in a gel receptor of a contact-type staining patch and only a proper amount of the staining sample is transferred to a specimen when the contact-type staining patch comes into contact with the specimen such that the contact-type staining patch can be used several times and the waste of staining samples can be prevented.

In addition, according to the present disclosure, there is no residue at a specimen when a contact-type staining patch comes into contact with the specimen such that a postprocessing process can be omitted.

In addition, according to the present disclosure, a contact-type staining patch transfers a staining sample to a specimen using a contacting means instead of a conventional spraying means such that staining may also be performed without fixing the specimen.

In addition, according to the present disclosure, when staining a specimen, various types of processes by which staining is accompanied can simply be performed by only bringing a contact-type staining supplementary patch into contact with the specimen such that an overall staining process can become extremely simple.

In addition, according to the present disclosure, when a staining sample is transferred to a specimen and then a buffering patch is brought into contact therewith, an optimal pH of the staining sample is satisfied such that staining performance can be improved. In addition, when the buffering patch is used, an excess amount of buffering solution is not transferred to the specimen such that there is almost no residue at the specimen and a washing or drying process can be omitted.

In addition, according to the present disclosure, fixing, mordanting, and decolorizing by which a staining process is accompanied can be conveniently performed using a fixating patch, a mordanting patch, and a decolorizing patch.

Effects of the present disclosure are not limited to those mentioned above, and unmentioned effects should be clearly understood by those of ordinary skill in the art to which the present disclosure pertains from the present specification and the accompanying drawings.

The description above is merely an illustrative description of the technical spirit of the present disclosure, and those of ordinary skill in the art to which the present disclosure pertains should be able to modify and change the present disclosure in various ways within a scope not departing from essential features of the present disclosure. Consequently, the embodiments of the present disclosure described above may also be implemented separate from each other or in combinations.

Consequently, the embodiments disclosed in the present disclosure are not limiting to the technical spirit of the present disclosure but describe the same, and the scope of the technical spirit of the present disclosure is not limited by the embodiments. The scope of the present disclosure should be construed by the claims below, and all technical ideas within the scope equivalent with the claims should be construed as belonging to the scope of the present disclosure.

What is claimed is:

1. A contact-type staining patch comprising:
   a staining solution having a staining substance configured to react with a specimen to be inspected; and
   a gel receptor provided as a gel matrix of a mesh structure in which a plurality of pores that contains the staining solution is formed and the mesh structure is configured to prevent the staining solution in the plurality of pores from leaking or degenerating, and having a contact surface that comes into contact with the specimen to transfer the staining substance to the specimen from the gel receptor, wherein the transferred staining substance reacts with the specimen,
   wherein the gel receptor is provided in a form of a column having a first surface as the contact surface, a second surface facing away from the first surface and a thickness as a distance between the first surface and the second surface, and the thickness is smaller than a length of the contact surface in a first direction.

2. The contact-type staining patch of claim 1, wherein:
   the staining solution includes the staining substance configured to react with the specimen and a solvent configured to create a reaction condition of the staining substance; and
   the gel receptor uses the mesh structure to maintain a reaction condition of the staining solution.

3. The contact-type staining patch of claim 1, wherein, in a process in which the staining solution is transferred to the specimen through the contact surface, the gel receptor inhibits excessive movement of the staining solution by using the mesh structure to prevent residue from remaining at the specimen.

4. The contact-type staining patch of claim 1, wherein the contact-type staining patch is a staining patch configured to assign a color to a specific component of the specimen, an antibody patch including an antibody that causes an antigen-antibody reaction with the specimen, or a DNA patch including a DNA probe that couples to a specific DNA sequence of the specimen.

5. The contact-type staining patch of claim 1, wherein the staining solution includes the staining substance selected from a staining substance that directly stains the specimen, a precipitation/aggregation inducing substance that either precipitates or aggregates the specimen, a fluorescent substance that allows the specimen to form a fluorescent color, an isotope that allows the specimen to be detected with radiation, and an enzyme attached to the specimen which secretes a detectable substance.

6. The contact-type staining patch of claim 5, wherein:
   the staining solution includes an attaching substance that is coupled to the staining substance and reacts with a specific component of the specimen to be attached to the specimen; and
   the attaching substance includes an antibody that causes an antigen-antibody reaction with the specimen or a DNA probe that has a sequence complementary to a specific DNA sequence of the specimen.

7. The contact-type staining patch of claim 1, wherein:
   the staining solution is provided in a liquid state; and
   the gel receptor is provided as hydrogel that inhibits a leakage of the staining solution in the liquid state to the outside.

8. The contact-type staining patch of claim 1, wherein:
   the staining solution includes a first staining sample that stains a specimen and a second staining sample that stains the specimen and is different from the first staining sample; and
   the part of the staining solution transferred to the specimen includes a part of the first staining sample and a part of the second staining sample.

* * * * *